United States Patent [19]
Garini et al.

[11] Patent Number: 5,906,919
[45] Date of Patent: May 25, 1999

[54] METHOD FOR CHROMOSOMES CLASSIFICATION

[75] Inventors: Yuval Garini, Mizpe Koranit; Nir Katzir, Givat Elah; David Wine; Dario Cabib, both of Timrat, all of Israel

[73] Assignee: Applied Spectral Imaging, Migdal Haemek, Israel

[21] Appl. No.: 08/962,845

[22] Filed: Nov. 3, 1997

Related U.S. Application Data

[62] Division of application No. 08/844,516, Apr. 18, 1997, Pat. No. 5,798,262, which is a continuation-in-part of application No. 08/635,820, Apr. 22, 1996, Pat. No. 5,817,462, which is a continuation-in-part of application No. 08/575,191, Dec. 20, 1995, which is a continuation-in-part of application No. 08/571,047, Dec. 12, 1995, Pat. No. 5,784,162, which is a continuation-in-part of application No. 08/392,019, Feb. 21, 1995, Pat. No. 5,539,517, which is a continuation-in-part of application No. 08/107,673, Aug. 18, 1993, abandoned, filed as application No. PCT/US92/01171, Feb. 19, 1992.

[51] Int. Cl.$^6$ .............................. C12Q 1/68; C12M 3/00; C12N 15/11; G02B 21/16
[52] U.S. Cl. ........................ 435/6; 435/287.2; 536/24.31; 359/368
[58] Field of Search .................... 435/6, 287.2; 359/368; 536/24.31

[56] References Cited

PUBLICATIONS

Reid et al. Simultaneous visualization of seven different DNA probes by in situ hybridization using combinatorial fluprescence and digital imaging microscopy. Proc. Natl. Acad. Sci. USA vol. 89 pages 1388–1392, 1992.

Primary Examiner—George C. Elliott
Assistant Examiner—John S. Brusca
Attorney, Agent, or Firm—Mark M. Friedman

[57] ABSTRACT

A method for finding L internal reference vectors for classification of L chromosomes or portions of chromosomes of a cell, the L chromosomes or portions of chromosomes being painted with K different fluorophores or combinations thereof, wherein K basic chromosomes or portions of chromosomes of the L chromosomes or portions of chromosomes are each painted with only one of the K different fluorophores, whereas the other L-K of the L chromosomes or portions of chromosomes are each painted with a different combination of the K different fluorophores, the method comprising the steps of (a) using a multi-band collection device for measuring a first vector for each pixel of each of the L chromosomes or portions of chromosomes; (b) identifying pixels belonging to each of the K basic chromosomes or portions of chromosomes and defining the pixels as basic pixels, so as to obtain K basic classes of basic pixels; (c) using at least one basic pixel from each of the K basic classes for obtaining K basic vectors, the K basic vectors being K internal reference vectors; (d) using the K basic vectors for identifying pixels belonging to the other L-K chromosomes or portions of chromosomes; and (e) using the pixels belonging to the other L-K chromosomes or portions of chromosomes for calculating the other L-K internal reference vectors, thereby finding all of the L internal reference vectors. A method for classification of L chromosomes or portions of chromosomes of a cell similarly painted using the above method for finding L internal reference vectors, and using the L reference vectors for classification of each of the pixels into one of L classification classes. And, images presenting color chromosomes.

25 Claims, 11 Drawing Sheets
(8 of 11 Drawing Sheet(s) Filed in Color)

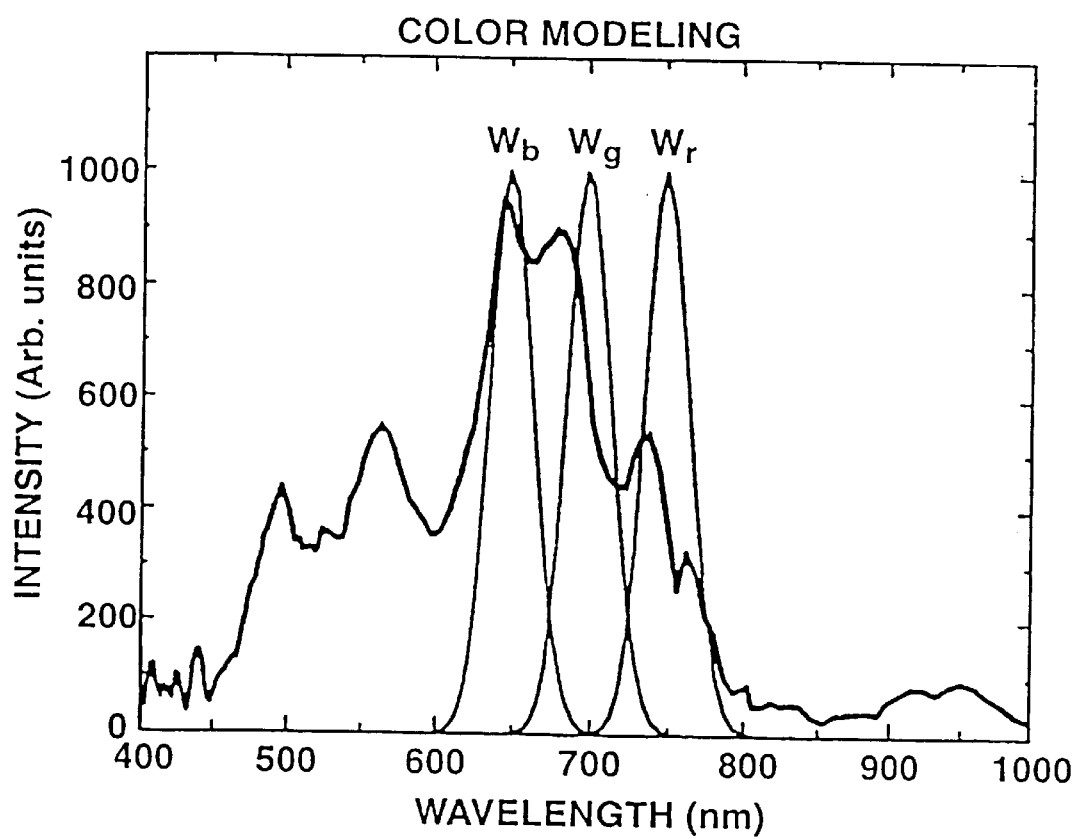

METHOD FOR CHROMOSOMES CLASSIFICATION

This is a divisional application of U.S. patent application Ser. No. 08/844,516, filed Apr. 18, 1997, now U.S. Pat. No. 5,798,262, which is a continuation-in-part of U.S. patent application Ser. No. 08/635,820, filed Apr. 22, 1996, U.S. Pat. No. 5,817,462, which is a continuation-in-part of U.S. patent application Ser. No. 08/575,191, filed Dec. 20, 1995, which is a continuation-in-part of U.S. patent application Ser. No. 08/571,047, filed Dec. 12, 1995, U.S. Pat. No. 5,784,162, which is continuation-in-part of U.S. patent application Ser. No. 08/392,019 filed Feb. 21, 1995, now U.S. Pat. No. 5,539,517, issued Jul. 23, 1996, which is a continuation-in-part of U.S. patent application Ser. No. 08/107,673, filed Aug. 18, 1992, now abandoned, filed as application No. PCT/US92/01171 filed Feb. 19, 1992. The specifications of each of these applications are hereby incorporated by reference.

FIELD AND BACKGROUND OF THE INVENTION

The present invention relates to classification of in situ painted chromosomes into a color (spectral) karyotype. More particularly, the present invention relates to a method for identifying prominent internal reference spectra to effect such classification.

The use of fluorescent dyes (i.e., fluorescent probes, fluorophores, fluorochromes, all are used interchangeably in this document), is one of the most powerful and common tools for analyzing tissues and cells. Fluorescence microscopy is therefore one of the most important experimental methods used in light microscopy [Lakowicz (1983) Principles of fluorescence spectroscopy, Plenuni Press, New York, London].

The power of fluorescent probes, is mainly due to the great variety of biological structures to which specific dyes can be bound [Waggoner (1986) Applications of fluorescence in the biomedical sciences, Eds. Taylor et al., New York: Alan R. Liss, Inc. pp. 3–28]. For a detailed review of fluorescent probes see, Mason, editor (1993) Fluorescent and Luminescent Probes for Biological Activity, Biological Techniques Series, edited by Sattelle, Academic Press Limited, London; and, Ploem and Tanke (1987) Introduction to Fluorescence Microscopy, Oxford University Press, Royal Microscopical Society.

The rapid development of new and more sophisticated multicolor fluorescent dye molecules continues to create a need for more advanced fluorescence imaging techniques that can utilize the full potential of these dyes. For a discussion of the revolutionary impact fluorescent dyes have had, and will continue to have, on the way research is conducted today, refer to Taylor et al. (1992) The New Vision of Light Microscopy, American Scientist, Vol. 80, pp. 322–335.

An important example where the detection of multiple fluorescent probes can be of significant advantage is FISH (fluorescent in situ hybridization) [Emanuel (1993) Growth Genetics and Hormones 9, pp. 6–12], which is used to analyze genes at the chromosome level, and find possible genetic defects such as gene/chromosome amplification, deletion, translocation, rearrangement and other abnormalities associated with genes and/or chromosomes.

Certain diseases and disorders, including many cancers and birth defects, are genetic disorders caused by defects (i.e., mutations) in one or more genes. Many other diseases are known or believed to have a genetic component(s), that is, there exists a genetic defect(s) that does not alone cause the disease but contributes to it, or increases the probability of developing the disease later in life, phenomena known in the art as multifactorial diseases and genetic predispositions.

Correlation of visible genetic defects with known diseases would allow physicians to make definitive diagnoses, and permit early detection and treatment of many diseases. Genetic counseling could alert prospective parents and at-risk individuals to the possibility of potentially serious medical problems in the future. permitting appropriate intervention.

More than 8,000 genetic disorders have now been identified, many of which are associated with multiple genetic defects. Following the discovery that chromosomes are the carriers of hereditary information. scientists reasoned that it should be possible to document visible defects in chromosomes that were responsible for specific disorders.

In the 1960's, staining techniques were developed for microscopy-based classification of metaphase chromosomes spreads. For several decades, visual analysis of chromosomes banding patterns has been used to correlate human genetic disorders with observed structural abnormalities in metaphase chromosomes. Chromosomes are typically examined by brightfield microscopy after Giemsa staining (G-banding), or by fluorescence microscopy after fluorescence staining (R-banding), to reveal characteristic light and dark bands along their length. Careful comparison of a patient's banding pattern with those of normal chromosomes can reveal abnormalities such as translocations (exchange of genetic material between or within chromosomes), deletions (missing chromosome(s) or fragment(s) thereof), additions, inversions and other defects that cause deformities and genetic diseases. Yet conventional chromosome banding techniques are limited in resolution.

Fluorescent in situ hybridization (FISH) has evolved over the past 25 years through the improvement of a number of complementary techniques. Its emergence has been driven by the desire of cytogeneticists to develop better tools for mapping the precise location of genes on chromosomes, and to detect very small genetic defects not visible by gross staining of chromosomes.

The human genome project (HGP), a bold initiative to identify and map all human genes, has identified interest in FISH and has hastened the development of much-needed DNA probes. Current FISH techniques have also been made possible by the concurrent development of powerful immunological probes, a growing variety of excellent fluorescent dyes for microscopy and spectroscopy, and dramatic improvements in the objectives, illuminators and filters used for fluorescence microscopy.

The power and utility of FISH is due to many factors: (1) FISH can be used not only on isolated chromosomes and nucleus, but also whole cells within fixed, paraffin-embedded tissue sections; (2) it can detect relatively small defects (ability of detecting smaller defects constantly increases); (3) it can provide results relatively fast; (4) its moderate cost allows it to be used in most diagnostic and research laboratories; (5) adaptation can be developed for various probes and specimen types; and, (6) high specificity and sensitivity can be achieved; (7) within a short time, typically in the range of two hours.

Many FISH applications merely require from the cytogeneticist to look through the eyepieces of a microscope, or at the image on the monitor, and to determine whether a fluorescent label is present or absent. With somewhat more complex specimens, a simple count of one or two colored labels may be done. However, the ability to process digital images and extract numerical data from them adds a vast new set of capabilities to FISH techniques.

An appropriate imaging method, can enhance very faint FISH images so that labeled chromosomes and loci are clearly identifiable. Under readily achieved experimental conditions, the number of labeled sites can be automatically counted. In addition, the intensity at each labeled site can be measured and the amount of DNA calculated to reveal, for example, the number of copies present of a particular gene.

As discussed above, FISH can provide information on the location of the labeled probe, the number of labeled sites on each chromosome, and the intensity of labeling (the amount of genetic material) at each site. Centromeric (repetitive DNA) probes and chromosome paints are used to tag and count the number of copies present of each targeted chromosome. Locus-specific probes are used to map the location of small regions of genetic material. These types of probes can be used on intact interphase nucleus as well as metaphase chromosome spreads, and can be counted visually or automatically by a suitable algorithm. They are routinely used to identify genetic diseases characterized by having too many or too few copies of a specific chromosome, chromosome fragment, or gene.

In very early stages of some cancers, long before the cells are recognized as abnormal, there may be an increase in the number of specific genes, phenomenon known in the art as gene amplification, that are detectable using locus-specific probes as homogeneously stained regions (HSR) and/or double minute chromosomes. Using FISH to detect chromosome abnormalities in cancerous cells may point out the developmental stage of the disease, and therefore to enable selecting the most suitable treatment(s), many of which are stage specific in their effectiveness.

It is possible to uniformly label the entire surface of one specific chromosome by isolating the chromosome (using flow cytometry, for example), physically (e.g., by sonication) or enzymatically (e.g., by endonucleases) chopping it up, and generating a set of probes against all of the fragments. Whole chromosome probes, also known as chromosome paints, fluorescently label all copies of their target chromosome. One important application of chromosome painting is the detection of translocation of genetic material between two chromosomes, as characteristically occurs in early stages of certain cancers, yet other chromosome aberrations are also detectable.

For example, if chromosome A is specifically labeled with a green paint and chromosome B is labeled with a red paint, translocation of genetic material from A to B will appear as a green area juxtaposed to a red area (and vice versa).

Typically, chromosome paints generated from normal chromosomes are used to detect deletions or translocations on abnormal (patient) chromosomes. Reverse chromosome painting uses probes generated from an abnormal chromosome to identify DNA from various normal chromosomes which contributed material to the abnormal chromosome.

The method of the present invention, as exemplified hereinbelow in the Examples section, enables to paint the 24 different chromosomes comprising the human karyotype (i.e., genome), each in a different color, and simultaneously detect, identify and meaningfully display a color human karyotype, using a single hybridization procedure followed by a single short measurement.

A remarked improvement in multicolor fluorescent dyes used for labeling chromosome paints is the introduction of combinatorial fluorescent strategies (e.g., combinatorial labeling and combinatorial hybridization) which employ various combinations of few basic fluorescent dyes. For further details on combinatorial labeling see, Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein. For further details about combinatorial hybridization see du-Manoir et al. (1993) Detection of complete and partial chromosome gains and losses by comparative genomic in situ hybridization. Hum. Genet. 90, 590–610, which is incorporated by reference as if fully set forth herein.

Numerous methods are available to label DNA probes for use in FISH assays, including indirect methods whereby a hapten such as biotin or digoxigenin is incorporated into DNA using enzymatic reactions. Following hybridization to a metaphase chromosome spread or interphase nucleus, a fluorescent label is attached to the hybrid through the use of immunological methods. More recently, fluorescent dyes have been directly incorporated into probes and detected without the use of an intermediate step. Standard FISH dyes include fluorescein, rhodamine, Texas-Red and cascade blue, and multiprobe FISH analysis can be accomplished by labeling different probes with different haptens or fluorescent dyes and combinations thereof, known in the art as combinatorial labeling [see, Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein]. Alternatively, a pool of a given probe may be divided into sub-pools, each labeled with a different fluorophore, after which the sub-pools are regrouped to yield otherwise similar hybridization results, a method known in the art as combinatorial hybridization [see, du-Manoir et al. (1993) Detection of complete and partial chromosome gains and losses by comparative genomic in situ hybridization. Hum. Genet. 90, 590–610, which is incorporated by reference as if fully set forth herein]. According to both labeling strategies obtained are combinatorial probes. Thus, when any of the terms "combination of fluorophores" or "combinatorial fluorescent strategy" is used herein in this document and especially in the claims below, it refers both to combinatorial labeling and to combinatorial hybridization, as described above.

The use of combinatorial fluorophores for chromosome painting and karyotyping, multicolor chromosome banding and comparative genome hybridization is described in details in U.S. Pat. No. 5,817,462, and in Science magazine [E. Schroeck et al. (1996) Multicolor spectral karyotyping of human chromosomes. Science, 273, 494–497], both are incorporated by reference as if fully set forth herein.

The main progress described in Science is that whole genome scanning by spectral imaging allows instantaneous visualization of defined emission spectra for each human chromosome after fluorescence in situ hybridization (FISH). By means of computer separation (classification) of spectra, spectrally-overlapping chromosome-specific DNA probes are resolved and all human chromosomes are simultaneously identified.

This spectral imaging approach therein described combines Fourier spectroscopy, charge coupled device (CCD)-imaging, and optical microscopy to measure simultaneously at all points in the sample emission spectra in the visible and near-infrared spectral range. This allows the use of multiple spectrally overlapping probes. The approach is based on the measurement of a discrete spectrum (identified from a sequence of intensities at every pixel measured at many different wavelengths), which facilitates the discrimination of multiple fluorophores. In dramatic contrast to conventional epifluorescence microscopy in which fluorochrome discrimination is based on the measurement of the fluorescence intensity through a small number of narrow band fluorochrome specific optical filters [see, Speicher et al. (1996) Nature Genetics. 12:368–375], the use of spectral karyotyping, as therein described, allows all the available information present in the emitted photons within the spectrum of emitted light, to be used for analysis.

The spectral-based method for discriminating spectrally overlapping fluorophores (classification) is readily extended to a large number of fluorochromes, provided there are measurable and consistent differences in the emission spectrum of each fluorochrome.

Simultaneous identification of each human chromosome in metaphase preparations, an approach referred to as spectral karyotyping, is also reported. To this end, chromosome-specific composite libraries generated by polymerase chain reaction (PCR) from flow-sorted human chromosomes are directly labeled with nucleotides conjugated to five different fluorophores or combinations thereof A composite probe set containing all 24 chromosomes is then hybridized to metaphase chromosomes. Chromosome-specific labeling is achieved by suppression hybridization. Specifically, repetitive sequences in the composite libraries are blocked by the addition of an excess of unlabeled human Cot-1 DNA.

The hybridization is presented in both RGB display and classification colors. Display colors allow all human chromosomes to be readily visualized after spectral imaging, and based on spectral measurements at each pixel, a chromosome classification algorithm is applied to spectrally karyotype all human chromosomes. One of the most important analysis algorithms is the spectral-based classification algorithm that enables multiple different spectra in the image to be identified and highlighted in classification-colors. This allows assignment of a specific classification-color to all human chromosomes based on their spectra. This algorithm assumes that the (reference) spectrum of each chromosome has been measured and stored in a reference library in the computer. A distinguishing classification-color is assigned to each pixel in the image according to the classification-color assigned to the reference spectrum that is most similar to the spectrum at that given pixel. A minimal square error algorithm as shown in Equation 1:

$$S_{x,y,n} = \int_{\lambda 1}^{\lambda 2} (I_{x,y}(\lambda) - I_n(\lambda))^2 d\lambda \quad (1)$$

is computed for every pixel, in which $I_{x,y}(\lambda)$ is the normalized spectrum at pixel coordinates x,y and $I_n(\lambda)$ represents the normalized reference spectrum for each of the chromosome n=1, 2, . . . , 23, 24. After calculating the value of $S_{x,y,n}$ for all reference spectra, the smallest value is chosen and an artificial classification-color is assigned to that pixel in accordance with the classification-color assigned to the most similar reference spectrum.

The potential of spectral karyotyping as a screening method for chromosomal aberrations was further explored by analyzing clinical samples from multiple laboratories where conventional banding methods or FISH with chromosome painting probes had been previously performed. In all cases, G-banding and spectral karyotyping revealed consistent results. In some cases, Giemsa-banding was not sufficient to entirely interpret the chromosomal aberrations. In these cases, the diagnosis of chromosomal aberrations by spectral karyotyping was confirmed with conventional dual-color FISH analysis. The smallest discernible aberration analyzed for this report was a translocation t(1;11) (q44;p15.3) in which the reciprocal translocation was unrecognizable by conventional banding analysis. The origin of the chromosomal material that contributed to the reciprocal translocation was correctly classified. The translocated segments on chromosomes 1 and 11 had been confirmed by subtelomere specific cosmid probes for chromosomes 1q and 11p. On the basis of the location of the probes utilized, the size of the alteration was estimated to be >1,500 kbp. In a second case, banding analysis suggested a translocation of a segment of chromosome 4 to chromosome 12. Spectral karyotyping unambiguously identified and classified the origin of the additional chromosomal material as being derived from chromosome 4. To determine the limit of sensitivity of spectral karyotyping, a case with a submicroscopic translocation (unrecognizable in both metaphase and prometaphase chromosomes) involving chromosomes 16 and 17 was examined. This t(16;17) had been previously demonstrated by FISH with cosmid probes and the reciprocal interchange of chromatin estimated at approximately 500 kbp. Spectral karyotyping with metaphase chromosomes from this patient failed to identify the known t(16;17) suggesting that the limit of sensitivity for metaphase chromosome analysis with currently available painting probes to be between 500–1,500 kbp.

To demonstrate that spectral karyotyping is an approach that can be used to complement conventional banding analysis, hybridization on previously G-banded chromosomes was performed. Probably due to the trypsin digestion that is required for G-banding, the signal intensity was slightly reduced as compared to metaphases that were not previously G-banded. The loss of signal intensity was approximately 10%, and could therefore easily be compensated for by prolonged exposure times. A slightly increased noise at the edges of previously G-banded chromosomes compared to non G-banded chromosomes was also observed. However, the classification of the metaphase could be readily achieved.

Thus, according to the above described approach, first, chromosomes of a single normal karyotype are identified by a conventional chromosome banding technique (e.g., G-banding or R-banding). Second, the same chromosomes are hybridized with chromosome paints as described above. Third, the average spectrum characterizing pixels attributed to any chromosome type (e.g., 1–22, X and Y in human male) as previously determined by chromosome banding is calculated and the resulting spectra (e.g., 24 for human) form a library of reference spectra. Fourth, the reference spectra are thereafter used for classification of pixels of new karyotypes into their chromosomes.

Nevertheless, as was experimentally observed, this approach is not always successful. In other words, in some cases new karyotypes do not appropriately classify. This is especially the case when abnormal or aberrant karyotypes, such as karyotypes of cancer cells, are analyzed. This may be due to one or more of the following reasons. First, differential hybridization efficiency. Second, chromosomes of different sources consistently behave in a different manner with respect to the hybridization, light emission, etc. And third, the measurement device is not identically calibrated in each measurement.

Nevertheless, it was further observed that when the reference spectra were used for karyotyping the chromosomes from which they were derived, best classification results were achieved. In other words, best results are achieved when the reference spectra employed are internal spectra. As described above, this, however, requires identification of the chromosomes via the conventional chromosome banding technique prior to classification. This, in turn, limits the scope of use of the classification method since (i) the method is not readily automateable; (ii) a highly trained cytogeneticist is required for analysis of the conventional banding pattern of the chromosomes; and (iii) in many cases of aberrant karyotypes, such as cancer cells karyotypes, the conventional banding pattern is not informative and therefore not conclusive.

The present invention is of a method for identifying more prominent reference spectra for chromosome classification, which reference spectra are calculated substantially automatically for each karyotype from spectral information derived from each karyotype. In other words, the present invention is of method for identifying internal reference spectra for chromosome classification, which reference spectra are calculated substantially automatically for each karyotype. Using internal reference spectra for classification overcomes the above described limitations of the prior art.

SUMMARY OF THE INVENTION

According to the present invention there is provided a method for classification of in situ painted chromosomes into a color (spectral) karyotype and a method for identifying prominent internal reference spectra to effect such classification.

According to further features in preferred embodiments of the invention described below, provided is a method for finding L internal reference vectors for classification of L chromosomes or portions of chromosomes of a cell, the L chromosomes or portions of chromosomes being painted with K different fluorophores or combinations thereof, wherein K basic chromosomes or portions of chromosomes of the L chromosomes or portions of chromosomes are each painted with only one of the K different fluorophores,, whereas the other L-K of the L chromosomes or portions of chromosomes are each painted with a different combination of the K different fluorophores, the method comprising the steps of (a) using a multi-band collection device for measuring a first vector for each pixel of each of the L chromosomes or portions of chromosomes; (b) identifying pixels belonging to each of the K basic chromosomes or portions of chromosomes and defining the pixels as basic pixels, so as to obtain K basic classes of basic pixels; (c) using at least one basic pixel from each of the K basic classes for obtaining K basic vectors, the K basic vectors being K internal reference vectors; (d) using the K basic vectors for identifying pixels belonging to the other L-K chromosomes or portions of chromosomes; and (e) using the pixels belonging to the other L-K chromosomes or portions of chromosomes for calculating the other L-K internal reference vectors, thereby finding all of the L internal reference vectors.

According to further features in preferred embodiments of the invention described below, provided is a method for classification of L chromosomes or portions of chromosomes of a cell, the L chromosomes or portions of chromosomes being painted with K different fluorophores or combinations thereof, wherein K basic chromosomes or portions of chromosomes of the L chromosomes or portions of chromosomes are each painted with only one of the K different fluorophores, whereas the other L-K of the L chromosomes or portions of chromosomes are each painted with a different combination of the K different fluorophores, the method comprising the steps of (a) finding L internal reference vectors by (i) using a multi-band collection device for measuring a first vector for each pixel of each of the L chromosomes or portions of chromosomes; (ii) identifying pixels belonging to each of the K basic chromosomes or portions of chromosomes and defining the pixels as basic pixels, so as to obtain K basic classes of basic pixels; (iii) using at least one basic pixel from each of the K basic classes for obtaining K basic vectors, the K basic vectors being K internal reference vectors; (iv) using the K basic vectors for identifying pixels belonging to the other L-K chromosomes or portions of chromosomes; and (v) using the pixels belonging to the other L-K chromosomes or portions of chromosomes for calculating the other L-K internal reference vectors, thereby finding all of the L internal reference vectors; and (b) using the L reference vectors for classification of each of the pixels into one of L classification classes.

According to further features in preferred embodiments of the invention described below, provided is a method for classification of L chromosomes or portions of chromosomes of a cell, the L chromosomes or portions of chromosomes being painted with K different fluorophores or combinations thereof. wherein K basic chromosomes or portions of chromosomes of the L chromosomes or portions of chromosomes are each painted with only one of the K different fluorophores, whereas the other L-K of the L chromosomes or portions of chromosomes are each painted with a different combination of the K different fluorophores, the method comprising the steps of (a) using a multi-band collection device for measuring a first vector for each pixel of each of the L chromosomes or portions of chromosomes; (b) identifying pixels belonging to each of the K basic chromosomes or portions of chromosomes and defining the pixels as basic pixels, so as to obtain K basic classes of basic pixels; (c) using at least one basic pixel from each of the K basic classes for obtaining K basic vectors, the K basic vectors being K internal reference vectors; and (d) using the K basic vectors for identifying pixels belonging to the other L-K chromosomes or portions of chromosomes.

According to still further features in the described preferred embodiments the method further comprising the step of attributing each of the classes of classified pixels a distinctive artificial color.

According to still further features in the described preferred embodiments provided is a method for classification of L chromosomes or portions of chromosomes of a cell, the L chromosomes or portions of chromosomes being painted with K different fluorophores or combinations thereof, wherein K basic chromosomes or portions of chromosomes of the L chromosomes or portions of chromosomes are each painted with only one of the K different fluorophores, whereas the other L-K of the L chromosomes or portions of chromosomes are each painted with a different combination of the K different fluorophores, the method comprising the steps of (a) using a multi-band collection device for measuring a first vector for each pixel of each of the L chromosomes or portions of chromosomes; (b) identifying pixels belonging to each of the K basic chromosomes or portions of chromosomes and defining the pixels as basic pixels, so as to obtain K basic classes of basic pixels; (c) using at least one basic pixel from each of the K basic classes for obtaining K basic vectors. the K basic vectors being K internal reference vectors; and (d) using the K basic vectors for identifying pixels belonging to the other L-K chromosomes or portions of chromosomes.

According to still further features in the described preferred embodiments provided is a method for classification of chromosomes or portions of chromosomes of a cell, the chromosomes or portions of chromosomes being painted with different fluorophores or combinations thereof, such that each of the chromosomes or portions of chromosomes being painted with a different fluorophore or combination of fluorophores, the method comprising the steps of (a) using a multi-band collection device for measuring a first vector for each pixel of each of the chromosomes or portions of chromosomes; (b) identifying pixels belonging to basic chromosomes or portions of chromosomes and defining the pixels as basic pixels, so as to obtain basic classes of basic pixels; (c) using at least one basic pixel from each of the basic classes for obtaining basic vectors, the basic vectors being basic internal reference vectors; and (d) using the basic internal reference vectors for identifying pixels belonging to the other chromosomes or portions of chromosomes.

According to still further features in the described preferred embodiments the classification of each of the pixels into one of the L classification classes using the L reference vectors is effected by a linear decomposition algorithm used for finding binary vectors for each of the pixels belonging to the L chromosomes or portions of chromosomes.

According to still further features in the described preferred embodiments provided is a method for detection of chromosome aberrations using the above method for chromosome classification.

According to still further features in the described preferred embodiments the multi-band collection device is selected from the group consisting of a spectral imager combined with one filter cube and a device including a plurality of additional filter cubes, and additional emission and excitation filters.

According to still further features in the described preferred embodiments each of the first vectors includes N items, N is an integer selected in the range of 3–150.

According to still further features in the described preferred embodiments each of the first vectors represents a spectrum.

According to still further features in the described preferred embodiments each of the first vectors is normalized.

According to still further features in the described preferred embodiments the identification of the pixels belonging to each of the K basic chromosomes or portions of chromosomes is effected by a method selected from the group consisting of (a) identifying the pixels belonging to each of the K basic chromosomes or portions of chromosomes using a conventional banding pattern of the L chromosomes or portions of chromosomes; (b) identifying the pixels belonging to each of the K basic chromosomes or portions of chromosomes using an RGB algorithm; and (c) identifying the pixels belonging to each of the K basic chromosomes or portions of chromosomes using K external basic vectors from a library.

According to still further features in the described preferred embodiments each of the K basic vectors is an average of a plurality of basic pixels belonging to one of the basic classes.

According to still further features in the described preferred embodiments the identification of the pixels belonging to each of the K basic chromosomes or portions of chromosomes using the external basic vectors from the library is effected by (a) employing a linear decomposition algorithm for defining for each pixel of the L chromosomes or portions of chromosomes a decomposition-K-vector; (b) using a high cut off value, for transforming each of the decomposition-K-vector into a transformed binary-K-vector; and (c) comparing each of the transformed binary-K-vector to K defined binary-K-vectors, defining each of the K different fluorophores, thereby identifying the pixels belonging to each of the K basic chromosomes or portions of chromosomes.

According to still further features in the described preferred embodiments the cell is of a human being.

According to still further features in the described preferred embodiments the identification of the pixels belonging to the other L-K chromosomes or portions of chromosomes and calculating the other L-K internal reference vectors is effected by (a) employing a linear decomposition algorithm for defining for each pixel of the L chromosomes or portions of chromosomes a decomposition-K-vector; (b) using a low cut off value or range, for transforming each of the decomposition-K-vector into a transformed binary-K-vector; and (c) comparing each of the transformed binary-K-vector to K-L defined binary-K-vectors, defining each of the combinations of the K different fluorophores, thereby identifying the pixels belonging to each of the L-K chromosomes or portions of chromosomes.

According to still further features in the described preferred embodiments provided is a display comprising an image of all chromosomes or portions of chromosomes of a cell, each of the chromosomes or portions of chromosomes being painted with a different fluorophore or a combination of fluorophores, the image presenting the chromosomes or portions of chromosomes in different distinctive colors, wherein each of the chromosomes or portions of chromosomes is attributed one of the different distinctive colors.

According to still further features in the described preferred embodiments provided is a display comprising a composite image of at least some chromosomes or portions of chromosomes of a cell, each of the chromosomes or portions of chromosomes being painted with a different fluorophore or a combination of fluorophores and banded with a chromosome banding technique to obtain a characteristic banding pattern (shading) for each of the chromosomes or portions of chromosomes, the image presenting the chromosomes or portions of chromosomes in distinctive colors, wherein each of the chromosomes or portions of chromosomes is attributed one of the distinctive colors and further wherein each of the distinctive colors is acquired an intensity pattern in accordance with the banding pattern of each of the chromosomes or portion of chromosomes, so that both the distinctive colors and the banding patterns of each of the chromosomes or portions of chromosomes are overlaid.

According to still further features in the described preferred embodiments provided is a display comprising a composite image of at least some chromosomes or portions of chromosomes of a cell, each of the chromosomes or portions of chromosomes being painted with a different fluorophore or a combination of fluorophores and banded with a chromosome banding technique to obtain a characteristic banding pattern and shape for each of the chromosomes or portions of chromosomes, the image presenting the chromosomes or portions of chromosomes in distinctive colors, wherein each of the chromosomes or portions of chromosomes is attributed one of the distinctive colors and further wherein each of the chromosomes or portion of chromosomes is acquired the characteristic shape, so that both the distinctive colors and the shapes of each of the chromosomes or portions of chromosomes are overlaid.

According to still further features in the described preferred embodiments provided is a display comprising a composite image of a chromosome or portion of chromosome, the chromosome or portion of chromosome being presented in a color, the color including a banding pattern of alternating lighter and darker bands, both the color and the pattern of bands being indicative of the chromosome portion of chromosome identification.

According to still further features in the described preferred embodiments provided is a display comprising an image of a chromosome or portion of chromosome, the chromosome or portion of chromosome being presented in a color, the color being indicative to the chromosome or portion of chromosome identification, wherein the chromosome or portion of chromosome being shaped similar to its shape when banded using a chromosome banding technique.

According to still further features in the described preferred embodiments provided is a display comprising a composite image of a chromosome or portion of chromosome, the composite image including a color image and a banded image of the chromosome or portion of chromosome.

The present invention successfully addresses the shortcomings of the presently known configurations by providing a method for chromosome classification which uses internal reference vectors for pixels classification, which internal reference vectors typically perform better. The method is readily automatable. Using this method will therefore enable semi or non-skilled cytogeneticists to acquire clear and informative karyotypes, which may include overlay of spectral and spatial information.

The file of this patent contains at least one drawing executed in color. Copies of this patent with color drawing (s) will be provided by the Patent and Trademark Office upon request and payment of the necessary fee.

BRIEF DESCRIPTION OF THE DRAWINGS

The invention herein described, by way of example only, with reference to the accompanying drawings, wherein:

FIG. 3c presents the arranged karyotype of the chromosomes of FIG. 3a;

FIG. 5 presents an example of weighting functions $w_r$, $w_g$, $w_b$ for the RGB algorithm;

DESCRIPTION OF THE PREFERRED EMBODIMENTS

Figure 1:
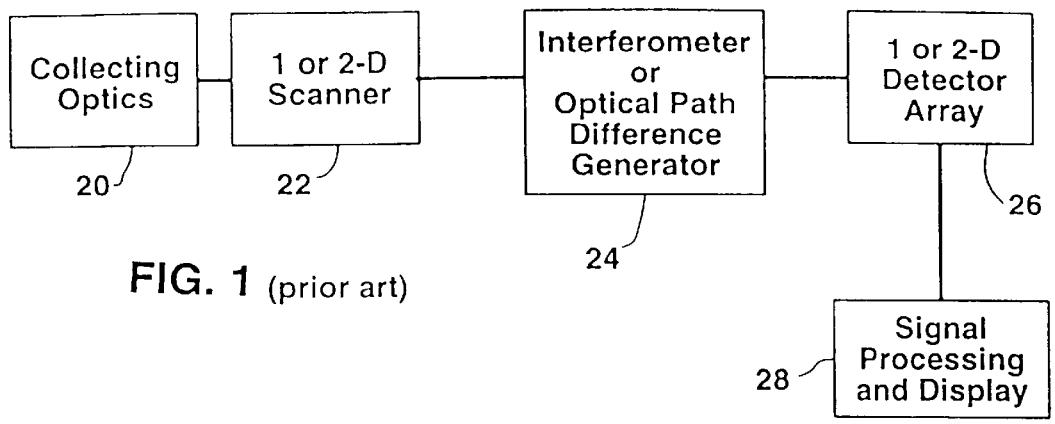
FIG. 1 is a block diagram illustrating the main components of an imaging spectrometer constructed in accordance with U.S. Pat. No. 5,539,517 (prior art)

The present invention is of a method for classification of in situ painted chromosomes into a color (spectral) karyotype which can be used to detect chromosomal aberrations. Specifically, the present invention relates to a method for identifying prominent internal reference spectra for such classification, the internal reference spectra are used to provide better classification results.

The principles and operation of the chromosome classification method according to the present invention may be better understood with reference to the drawings and accompanying descriptions.

Spectral imaging is the technology that enables the measurement of the spectrum of light emitted by every point (pixel) of an object. A spectral imager (also referred herein as imaging spectrometer) is an instrument that measures and stores in memory for later retrieval and analysis the spectrum of light emitted by every point of the object which is placed in its field of view. A spectral image is a collection of spectra of the object measured by a spectral imager. It is usually organized as an intensity function defined in a three dimensional space in which two dimensions are of an image (x and y), and one is of a spectral axis ($\lambda$). As such, a spectral image is usually referred to as a "cube" of data or "spectral cube".

The spectrum of each pixel is in fact an N-vector, wherein N is an integer which depends upon the spectral range and the spectral resolution of the imager.

Prior art teaches different methods of measuring spectral images (i.e. spectral cubes). Devices designed according to these methods typically include light collection optics; a dispersion element (e.g., a grating or a prism), filter(s) (e.g., AOTF or LCTF) or an interferometer; focusing optics; and a two-dimensional array of detectors (typically a CCD in the visible range and other types of detectors in the infrared range).

Each method has advantages and disadvantages, however as shown in U.S. Pat. No. 5,539,517, issued Jul. 23, 1996, and in Journal of Microscopy [Vol. 182, pp. 133–140, 1996], both are incorporated by reference as if fully set forth herein, a spectral imager based on a special type of triangular interferometer has advantages of sensitivity, compactness and stability that more conventional spectral imagers do not have. It should however be noted that an N vector for each pixel can also be obtained using narrow band and/or wide band emission filters combined with suitably selected excitation filters which all match the fluorophores employed. One can thus obtain intensity values with each of the emission filters for each of the pixels, which values form an N vector for each pixel, wherein N equals the number of emission filters employed. Unless a single excitation filter is employed in combination with all emission filters, this vector is not what would have been considered a low resolution spectral vector. However, careful selection of the filters and the fluorophores enables to obtain N vectors which enable to differentiate among the fluorophores. Therefore, the classification procedure as herein described applies also to these vectors.

A method for chromosome classification using principally narrow band filters is disclosed in Speicher R. M., Ballard S. G. and Ward C. D. (1996) Karyotyping human chromosomes by combinatorial multi-flour FISH. Nature genetics, 12:368–375, which is incorporated by reference as if fully set forth herein. In this case the number of excitation filters is six and therefore the N vectors measured are in fact 6-vectors.

A spectral imager in accordance with the invention disclosed in U.S. Pat. No. 5,539,517 was developed by Applied Spectral Imaging Ltd., Industrial Park, Migdal Haemek, Israel and is referred hereinbelow as SpectraCube™. This instrument may provide N vectors wherein N equals about 30–50, typically 40, in the visible range.

The importance of a spectral image measurement resides in the fact that the spectrum of light carries information about the composition of matter of which the object is made, and therefore it can be used to map and visualize phenomena which cannot be seen or distinguished otherwise. As a color image is the next step after a io black and white image, a spectral image is the next step after a color image. Similarly to the difference of green hues between the leaves of two different types of trees or between a young leaf and an old one, two fluorescent dyes such as Texas Red and Rhodamine appear the same color to the human eye but they are well distinguished by a spectrograph with ten nanometers resolution. A complex biological system such as the white blood cell stained with Giemsa, looks to the eye through the microscope in transmission of white light, as an object with structures composed of regions of purple, blue and reddish colors in different levels of intensity. Since the colors as perceived by the human eye are composed of combinations of only three colors, red, green and blue (RGB), the number of different regions in the cell that can be classified by color is limited. For each point of the same cell a spectral imager measures a spectrum or other vector which depends on the chemical materials present at that point, and this is a function of wavelength which contains the order of fifty data (depending on spectral resolution) instead of only three as for a color image. As a result, small spectral differences or shifts between pixels can be distinguished by a spectral imager, which the eye would recognize as belonging to the same color, and therefore many more classes of biological structures or components can be distinguished in the cell using a spectral imager, as compared with the human eye.

For example, in Fluorescence Imaging Spectroscopy and Microscopy, edited by X. F. Wang and B. Herman, Vol. 137 pp. 87–124, 1996, John Wiley & Sons, a nuclear wall is shown sharply distinct from the rest of the nucleus in a spectral image, contrary to a simple color image where the wall is perceived as part of the nucleus (see ibidem FIG. 4.10$d$ on page 115).

In E. Schroeck et al. (1996) Multicolor spectral karyotyping of human chromosomes. Science, 273, 494–497, it is shown how a spectral imager as disclosed in U.S. Pat. No. 5,539,517 is used in combination with fluorescence in situ hybridization (FISH) techniques to analyze combinatorially painted chromosomes (human and animals), so that karyotyping and chromosomal aberrations can be detected and characterized.

According to this technique, which is further described in the background section hereinabove and in the Examples section below, each chromosome is hybridized with complementary DNA material which contains a different combination of fluorescent dyes out of a larger set of dyes, such that each chromosome of a metaphase spread emits a different fluorescence spectrum substantially uniformly over its surface. Typically, each chromosome is labeled with a different combination of up to four dyes (e.g., one, two, three or four dyes) selected from a set of five dyes, resulting in 24 different fluorescence spectra, one for each chromosome. This is done with human (requiring 24 different spectra or 24 combinations of dyes), mouse and monkey chromosomes (for which the number is different than 24), and with healthy and diseased (e.g., cancerous) cells. The detection and identification of translocations while using this method is immediate and reliable because the different spectrum of a translocation stands out clearly in the surrounding chromosome, whereas the information carried by the G-banding technique, widely used today for chromosome classification, is much less obvious for this purpose.

The terms "spread" and "karyotype" are interchangeably used in this document to indicate the visualization of chromosomes. In most cases the term "spread" is used to indicate chromosomes before their rearrangement into chromosome pairs and the term "karyotype" is used to indicate chromosomes after such arrangement, however, this is not intended to limit the identical meaning of these terms, which refer to a set of chromosomes, each of which is identified.

However, as further described in the background section above, the classification method therein employed is based on universal reference spectra, derived from a normal karyotype, which is thereafter used for classification of chromosomes in other karyotypes. As further mentioned above, this approach is not always successful, as in some cases new karyotypes do not appropriately classify, or classify only partially.

Since best classification results are obtained using internal reference spectra, the present invention is directed at providing a method of calculating internal reference spectra, which calculation is independent of pre-classification using standard chromosome classification techniques (e.g., G-banding or R-banding), as is the case in the prior art.

Thus, according to the present invention provided is a method for finding L internal reference vectors for classification of L chromosomes or portions of chromosomes of a cell. The term "chromosomes or portions of chromosomes" as used herein and in the claims refers to chromosomes or portions of chromosomes derived from the L kinds or types of chromosomes present in a cell, or any fraction or subset of those chromosomes. However, each of the types is typically present in two copies. In some pathological cases (e.g., cancer) chromosomal aberrations result in having type(s) of chromosome(s) present in more or less than two copies, wherein portions or full chromosomes are, for example, duplicated or missing. Should the cell selected be of a human being and if all the chromosomes are analyzed, in most cases, L would equal 24 for male and 23 for female.

However, the invention is also directed at analyzing a subset of the chromosomes of a cell, therefore "L" may be any integer smaller than the number of chromosomes characterizing the analyzed cell. Further according to the method, the L chromosomes or portions of chromosomes are painted with K, say 5, different fluorophores or combinations thereof, wherein IK basic chromosomes or portions of chromosomes of the L chromosomes or portions of chromosomes are each painted with only one of the K different fluorophores, whereas the other L-K, say 19 for human male, of the L chromosomes or portions of chromosomes are each painted with a different combination of the K different fluorophores. Painting of the chromosomes is effected using a combinatorial labeling approach which may be, for example, combinatorial labeling or combinatorial hybridization as further described herein. Preferably combinatorial hybridization is of choice.

The steps of the method are as follows. A multi-band collection device is used for measuring a first vector for each pixel of each of the L chromosomes or portions of chromosomes. Thereafter, pixels belonging to each of the K basic chromosomes or portions of chromosomes are identified and the pixels defined as basic pixels, so as to obtain K basic classes of basic pixels. At least one basic pixel from each of the K basic classes is used for obtaining K basic vectors, the K basic vectors being K internal reference vectors. The K basic vectors are then used for identifying pixels belonging to the other L-K chromosomes or portions of chromosomes. Finally, the pixels belonging to the other L-K chromosomes or portions of chromosomes are used for calculating the other L-K internal reference vectors, thereby finding all of the L [K+(L-K)] internal reference vectors.

For most applications K may equal 5. However, other combinations of fluorophores are also applicable, depending on their type, spectral characteristics and the number of chromosomes or portions of chromosomes analyzed, L.

According to a preferred embodiment of the invention, the method above described is used for classification of L chromosomes or portions of chromosomes of a cell. To this end the chromosomes are painted with K different fluorophores or combinations thereof as described above. For chromosome classification, L internal reference vectors are found as described above and are used for classification of each of the pixels into one of L classification classes.

In a preferred embodiment of the invention, classes of classified pixels are each attributed a distinctive artificial color. Preferably, the classification of each of the pixels into one of the L classification classes using the L reference vectors is effected by a linear decomposition algorithm used for finding binary vectors for each of the pixels belonging to the L chromosomes or portions of chromosomes, all as further described hereinbelow in the Examples section. The method for chromosome classification may be employed for the detection of chromosome aberrations.

According to further features in preferred embodiments of the invention described below, provided is a method for classification of L chromosomes or portions of chromosomes of a cell, the L chromosomes or portions of chromosomes being painted with K different fluorophores or combinations thereof, wherein K basic chromosomes or portions of chromosomes of the L chromosomes or portions of chromosomes are each painted with only one of the K different fluorophores, whereas the other L-K of the L chromosomes or portions of chromosomes are each painted with a different combination of the K different fluorophores, the method comprising the steps of (a) using a multi-band collection device for measuring a first vector for each pixel of each of the L chromosomes or portions of chromosomes; (b) identifying pixels belonging to each of the K basic chromosomes or portions of chromosomes and defining the pixels as basic pixels, so as to obtain K basic classes of basic pixels; (c) using at least one basic pixel from each of the K basic classes for obtaining K basic vectors, the K basic vectors being K internal reference vectors; and (d) using the K basic vectors for identifying pixels belonging to the other L-K chromosomes or portions of chromosomes.

According to still further features in the described preferred embodiments the method further comprising the step of attributing each of the classes of classified pixels a distinctive artificial color.

Classification of chromosomes according to the present invention may be effected by basic pixels based classification, wherein the step of identifying th internal reference vectors is skipped. According to this embodiment, provided is a method for classification of L chromosomes or portions of chromosomes of a cell, painted with K different fluorophores or combinations thereof as above described, the method includes the steps of (a) using a multi-band collection device for measuring a first vector for each pixel of each of the L chromosomes or portions of chromosomes; (b) identifying pixels belonging to each of the K basic chromosomes or portions of chromosomes and defining the pixels as basic pixels, so as to obtain K basic classes of basic pixels; (c) using at least one basic pixel from each of the K basic classes for obtaining K basic vectors, the K basic vectors being K internal reference vectors; and (d) using the K basic vectors for identifying pixels belonging to the other L-K chromosomes or portions of chromosomes.

As further described under Example 3 below, in some cases the basic chromosomes or portions of chromosomes, and therefore the basic pixels and reference vectors are associated with more than a single fluorophore. Therefore, further according to the present invention, provided is a method for classification of chromosomes or portions of chromosomes of a cell, the chromosomes or portions of chromosomes being painted with different fluorophores or combinations thereof, such that each of the chromosomes or portions of chromosomes being painted with a different fluorophore or combination of fluorophores, the method comprising the steps of (a) using a multi-band collection device for measuring a first vector for each pixel of each of the chromosomes or portions of chromosomes; (b) identifying pixels belonging to basic chromosomes or portions of chromosomes and defining the pixels as basic pixels, so as to obtain basic classes of basic pixels; (c) using at least one basic pixel from each of the basic classes for obtaining basic vectors, the basic vectors being basic internal reference vectors; and (d) using the basic internal reference vectors for identifying pixels belonging to the other chromosomes or portions of chromosomes.

Preferably, the multi-band collection device is either a spectral imager combined with one filter cube and a device including a plurality of additional filter cubes, and additional emission and excitation filters., as further hereinabove described.

Still Preferably, each of the first vectors mentioned above includes N items, N is an integer selected in the range of 3–150, which is preferably normalized, as further detailed in the Examples section below. Still preferably, each of the first vectors represents a spectrum.

In a preferred embodiment of the invention the identification of the pixels belonging to each of the K basic chromosomes or portions of chromosomes is effected by a method such as identifying the pixels belonging to each of the K basic chromosomes or portions of chromosomes using a conventional banding pattern of the L chromosomes or portions of chromosomes. Or such as identifying the pixels belonging to each of the K basic chromosomes or portions of chromosomes using an RGB algorithm. Alternatively, such as identifying the pixels belonging to each of the K basic chromosomes or portions of chromosomes using K external basic vectors from a library. In any case, preferably, each of the K basic vectors is an average of a plurality of basic pixels belonging to one of the basic classes.

In another preferred embodiment of the invention the identification of the pixels belonging to each of the K basic chromosomes or portions of chromosomes using the external basic vectors from the library is effected by (a) employing a linear decomposition algorithm for defining for each pixel of the L chromosomes or portions of chromosomes a decomposition-K-vector; (b) using a high cut off value, for transforming each of the decomposition-K-vector into a transformed binary-K-vector; and (c) comparing each of the transformed binary-K-vector to K defined binary-K-vectors, defining each of the K different fluorophores, thereby identifying the pixels belonging to each of the K basic chromosomes or portions of chromosomes.

In yet another preferred embodiment of the invention the identification of the pixels belonging to the other L-K chromosomes or portions of chromosomes and calculating the other L-K internal reference vectors is effected by (a) employing a linear decomposition algorithm for defining for each pixel of the L chromosomes or portions of chromosomes a decomposition-K-vector; (b) using a low cut off value or range, for transforming each of the decomposition-K-vector into a transformed binary-K-vector; and (c) comparing each of the transformed binary-K-vector to L-K defined binary-K-vectors, defining each of the combinations of the K different fluorophores, thereby identifying the pixels belonging to each of the L-K chromosomes or portions of chromosomes.

Further according to the invention provided are colored chromosome karyotypes. One such colored karyotype is a display which includes an image of all chromosomes or portions of chromosomes of a cell. Each of the chromosomes or portions of chromosomes is painted with a different fluorophore or a combination of fluorophores. The image presents the chromosomes or portions of chromosomes in different distinctive colors, wherein each of the chromosomes or portions of chromosomes is attributed one of the different distinctive colors. The term "display" as used herein refers to any visual presentation such as, but not limited to, a photograph, a print, screen display or monitor display.

Another color karyotype of the invention is a display which includes a composite image of at least some chromosomes or portions of chromosomes of a cell. Each of the chromosomes or portions of chromosomes is painted with a different fluorophore or a combination of fluorophores and banded with a chromosome banding technique for obtaining a characteristic banding pattern for each of the chromosomes or portions of chromosomes. The image presents the chromosomes or portions of chromosomes in distinctive colors, wherein each of the chromosomes or portions of chromosomes is attributed one of the distinctive colors and further wherein each of the distinctive colors is acquired an intensity pattern in accordance with the banding pattern of each of the chromosomes or portion of chromosomes, so that both the distinctive colors and the banding patterns of each of the chromosomes or portions of chromosomes are overlaid.

Yet another color karyotype of the invention is a display which includes a composite image of at least some chromosomes or portions of chromosomes of a cell. Each of the chromosomes or portions of chromosomes is painted with a different fluorophore or a combination of fluorophores and banded with a chromosome banding technique for obtaining a characteristic banding pattern and shape for each of the chromosomes or portions of chromosomes. The image presents the chromosomes or portions of chromosomes in distinctive colors, wherein each of the chromosomes or portions of chromosomes is attributed one of the distinctive colors and further wherein each of the chromosomes or portion of chromosomes is acquired the characteristic shape, so that both the distinctive colors and the shapes of each of the chromosomes or portions of chromosomes are overlaid.

Further according to the presented invention provided is a display which includes a composite image of a chromosome or portion of chromosome. The chromosome or portion of chromosome is presented in a color, the color including a banding pattern of alternating lighter and darker bands. Wherein, both the color and the pattern of bands are each indicative of the chromosome portion of chromosome identification (i.e., chromosome number and/or region).

Still further according to the presented invention provided is a display which includes an image of a chromosome or portion of chromosome. The chromosome or portion of chromosome is presented in a color which is indicative to the chromosome or portion of chromosome identification. Wherein, the chromosome or portion of chromosome is shaped similar to its shape (out line) when banded using a chromosome banding technique (e.g., G-banding, R-banding (DAPI), etc.).

Yet, further according to the presented invention provided is a display which includes a composite image of a chromosome or portion of chromosome, the composite image including overlay of a color image and a banded image of the chromosome or portion of chromosome.

The method of the present invention has major advantages over prior art methods, due to the introduction of chromosome classification which uses internal reference vectors for pixels classification, which internal reference vectors typically perform better. Another advantage of the present invention is that the method is readily automated. Using this method will therefore enable semi or non-skilled cytogenetecists to acquire clear and informative karyotypes, which may include overlay of spectral and spatial information.

Reference is now made to the following examples, which together with the above descriptions, illustrate the invention in a non limiting fashion.

EXAMPLE 1

Chromosomes Preparation for Measurement

The emergence of multicolor FISH has broadened the applications of molecular cytogenetics in basic research and genetic diagnosis. All existing multicolor FISH techniques require the use of fluorescent probes whose emission spectra can be separated with optical filters [Ried et al., (1992) Simultaneous visualization of seven different DNA probes by in, situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein]. This requirement limits the number of dyes which can be distinguished in a given sample.

A novel approach for FISH, employing the SpectraCube™ system to measure and analyze multiple spectrally overlapping labeled probes (single and combinatorial), to classify chromosomes and therefore to detect chromosomal aberrations was recently introduced [E. Schroeck et al. (1996) Multicolor spectral karyotyping of human chromosomes. Science, 273, 494–497].

According to this novel approach, spectral bio-imaging which is a combination of Fourier spectroscopy, CCD-imaging and optical microscopy enabling the measurement of accurate spectral data simultaneously at all points of a biological sample, was used to visualize hybridization based multicolor appearance of all (i.e., 24) types of human chromosomes and to generate a color map of the human karyotype (a color/spectral karyotype).

Following is a description of the dyes and their combinations which are presently preferred, which dyes and combinations were used to implement the chromosome classification method of the present invention.

Thus, 24 chromosome paints (1 through 22, X and Y, Table 1), each labeled with a different combination of four or less different flourophores selected from a set of five fluorophores according to the combinatorial hybridization approach (a through e, Table 1), (see Table 1 for the different fluorophores and their spectral characteristics and Table 2 for the assignment of the fluorophores listed in Table 1 to obtain the 24 chromosome paints), were simultaneously hybridized with human mitotic chromosome spreads of few non-related male white blood cells, prepared for hybridization essentially as described in Ried et al. [Ried et al., (1992) Simultaneous visualization of seven different DNA probes by in situ hybridization using combinatorial fluorescence and digital imaging microscopy. Proc. Natl. Acad. Sci. USA 89, 1388–1392].

Hybridized chromosomes were viewed through an inverted fluorescence microscope connected to the SpectraCube™ System and were analyzed.

It is clear to one ordinarily skilled in the art that other fluorophores, other combinations of fluorophores and different labeling approaches (e.g., combinatorial labeling) can be similarly used. Thus the body of information listed hereinbelow in Tables 1 and 2 is of an illustrative nature only, and there is no intention to limit the scope of the invention to the listed fluorophores, combinations of fluorophores and/or labeling technique.

TABLE 1

| Fluorophore | Symbol | Excitation (nm) |
| --- | --- | --- |
| Spectrum Orange | a | 540–580 |
| Texas-Red | b | 540–570 |
| Cy5™[1] | c | 630–670 |
| Spectrum Green | d | 475–495 |
| Cy5.5™[1] | e | 630–670 |

[1]from Amersham

TABLE 2

| Chromosome | Chromosome paint | Fluorophores |
| --- | --- | --- |
| human chromosome 1 | 1 | b, c, d |
| human chromosome 2 | 2 | e |

TABLE 2-continued

| Chromosome | Chromosome paint | Fluorophores |
| --- | --- | --- |
| human chromosome 3 | 3 | a, c, d, e |
| human chromosome 4 | 4 | c, d |
| human chromosome 5 | 5 | a, b, d, e |
| human chromosome 6 | 6 | b, c, d, e |
| human chromosome 7 | 7 | b, c |
| human chromosome 8 | 8 | d |
| human chromosome 9 | 9 | a, d, e |
| human chromosome 10 | 10 | c, e |
| human chromosome 11 | 11 | a, c, d |
| human chromosome 12 | 12 | b, e |
| human chromosome 13 | 13 | a, e |
| human chromosome 14 | 14 | b |
| human chromosome 15 | 15 | a, b, c |
| human chromosome 16 | 16 | b, d |
| human chromosome 17 | 17 | c |
| human chromosome 18 | 18 | a, b, d |
| human chromosome 19 | 19 | a, c |
| human chromosome 20 | 20 | a |
| human chromosome 21 | 21 | d, e |
| human chromosome 22 | 22 | b, c, e |
| human chromosome X | X | a, e |
| human chromosome Y | Y | c, d, e |

EXAMPLE 2

The Measurement Apparatus

FIG. 1 is a block diagram illustrating the main components of a prior art imaging spectrometer disclosed in U.S. Pat. No. 5,539,517, issued Jul. 23, 1996, which is incorporated by reference as if fully set forth herein. This imaging spectrometer is constructed highly suitable to implement the method of the present invention as it has high spectral (Ca. 4–14 nm depending on wavelength) and spatial (Ca. 30/M $\mu$m where M is the effective microscope or fore optics magnification) resolutions.

Thus, the prior art imaging spectrometer of FIG. I includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously for all the pixels of the field of view, in order to obtain all the information required to reconstruct the spectrum. The spectra of all the pixels in the scene are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517 alternative types of interferometers may be employed. These include (1) a moving type interferometer in which the OPD is varied to modulate the light, namely, a Fabry-Perot interferometer with scanned thickness; (2) a Michelson type interferometer which includes a beamsplitter receiving the beam from an optical collection system and a scanner, and splitting the beam into two paths; (3) a Sagnac interferometer optionally combined with other optical means in which interferometer the OPD varies with the angle of incidence of the incoming radiation, such as the four-mirror plus beamsplitter interferometer as further described in the cited U.S. patent (see FIG. 14 there).

Figure 2:
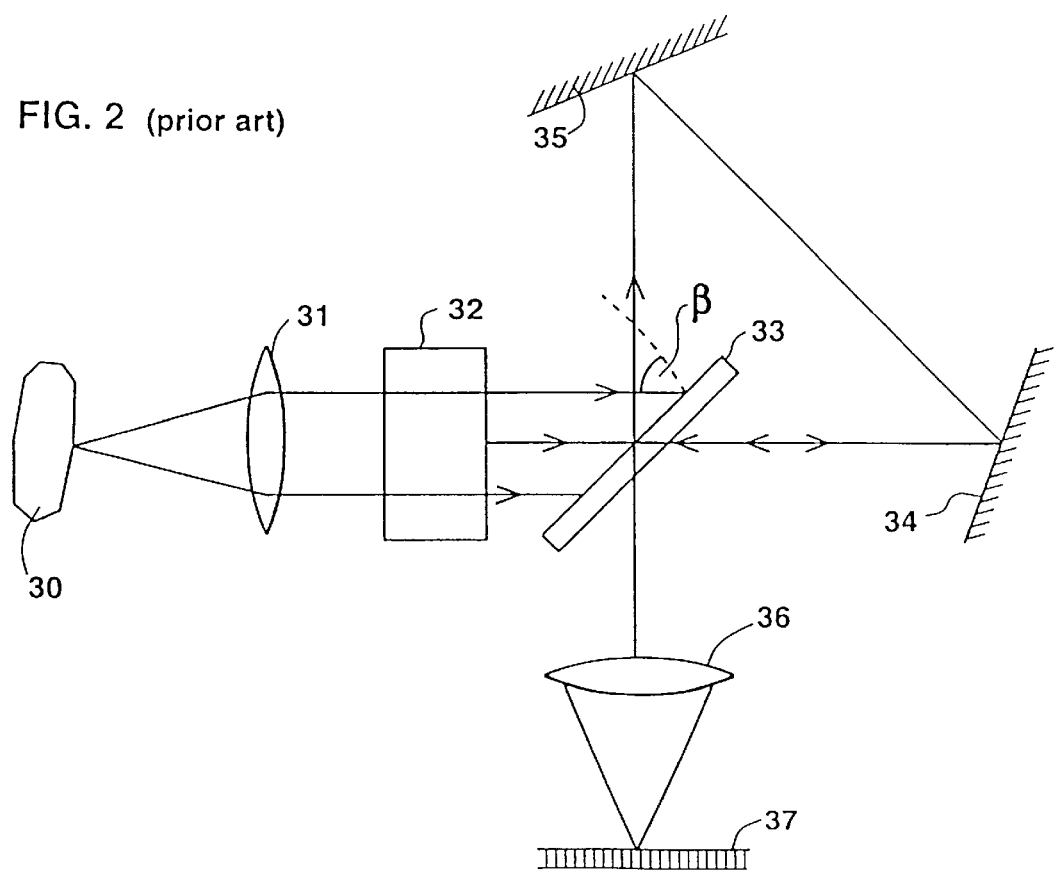
FIG. 2 illustrates a Sagnac interferometer, as used in an imaging spectrometer in accordance with U.S. Pat. No. 5,539,517 (prior art)

FIG. 2 illustrates an imaging spectrometer constructed in accordance with U.S. Pat. No. 5,539,517, utilizing an interferometer in which the OPD varies with the angle of incidence of the incoming radiation. A beam entering the interferometer at a small angle to the optical axis undergoes an OPD which varies substantially linearly with this angle.

In the interferometer of FIG. 2, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

At the end of one scan, every pixel has been measured through all the OPD's, and therefore the spectrum of each pixel of the scene can be reconstructed by Fourier transformation. A beam parallel to the optical axis is compensated, and a beam at an angle ($\theta$) to the optical axis undergoes an OPD which is a function of the thickness of the beamsplitter 33, its index of refraction, and the angle $\theta$. The OPD is proportional to $\theta$ for small angles. By applying the appropriate inversion, and by careful bookkeeping, the spectrum of every pixel is calculated.

In the configuration of FIG. 2 the ray which is incident on the beamsplitter at an angle $\beta$ ($\beta=45°$ in FIG. 2) goes through the interferometer with an OPD=0, whereas a ray which is incident at a general angle $\beta-\theta$ undergoes an OPD given by Equation 2:

$$OPD(\beta,\theta,t,n)=t[(n^2-\sin^2(\beta+\theta))^{0.5}-(n^2-\sin^2(\beta-\theta))^{0.5}+2\sin\beta\sin\theta]$$

where $\theta$ is the angular distance of a ray from the optical axis or interferometer rotation angle with respect to the central position; t is the thickness of the beamsplitter; and n is the index of refraction of the beamsplitter.

It follows from Equation 2 that by scanning both positive and negative angles with respect to the central position, one gets a double-sided interferogram for every pixel, which helps eliminate phase errors giving more accurate results in the Fourier transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact., according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Thus, imaging spectrometers constructed in accordance with the invention disclosed in U.S. Pat. No. 5,539,517 do not merely measure the intensity of light coming from every pixel in the field of view, but also measure the spectrum of each pixel in a predefined wavelength range. They also better utilize all the radiation emitted by each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including medical diagnostic and therapy and biological research applications, as well as remote sensing for geological and agricultural investigations, and the like.

As mentioned above, an imaging spectrometer in accordance with the invention disclosed in U.S. Pat. No. 5,539,517 was developed by Applied Spectral Imaging Ltd., Industrial Park, Migdal Haemek, Israel and is referred herein as SpectraCube™.

The SpectraCube™ system optically connected to a microscope is used to implement the method for chromosome classification of the present invention. The SpectraCube™ system has the following or better characteristics, listed hereinbelow in Table 3:

TABLE 3

| Parameter | Performance |
| --- | --- |
| Spatial resolution: | 30/M $\mu$m (M = effective microscope or fore optics magnification) |
| Field of View: | 15/M millimeters |
| Sensitivity: | 20 milliLux (for 100 msec integration time, increases for longer integration times linearly with $\sqrt{T}$) |
| Spectral range: | 400–1000 nm |
| Spectral resolution: | 4 nm at 400 nm (16 nm at 800 nm) |
| Acquisition time: | 5–50 sec, typical 25 sec |
| FFT processing time: | 20–180 sec, typical 60 sec |

The prior art SpectraCube™ system is used herein to acquire an N vector of spectral data (a spectrum in this case) of every pixel of metaphase in situ painted chromosomes as described above. However, as specified above, any spectral imager. i.e., an instrument that measures and stores in memory for later retrieval and analysis the spectrum of light emitted by every point of an object which is placed in its field of view, including filter (e.g., acousto-optic tunable filters (AOTF) or liquid-crystal tunable filter (LCTF)) and dispersive element (e.g., grating or prism) based spectral imagers, or other spectral data or multi-band collection devices (e.g., a device in accordance with the disclosure in Speicher R. M., Ballard S. G. and Ward C. D. (1996) Karyotyping human chromosomes by combinatorial multiflour FISH. Nature genetics, 12:368–375) can be used to acquire the required spectral data. Therefore, it is intended not to limit the scope of the present invention for use of any specific type of spectral data collection devices, nor any specific type of spectral imager.

EXAMPLE 3

Identification of Internal Reference Vectors for Chromosome Classification

1. Definitions and Preliminary Treatment of the Spectral Data

A spectrum can be represented as a N size-vector in which each component or item represents the intensity of light at a selected wavelength. The number of components (N) of which a spectrum is composed depends on the spectral range (e.g., visible light range, 400–750 nm) and the spectral resolution of the measurement apparatus. For example, with a 2 nm spectral resolution homogeneously distributed over a spectral range of, say, 400 nm to 700 nm, a spectrum is represented by a 151-vector.

Therefore, when the term "spectrum" (or spectra in plural) is used in the specification and claims below, it refers to the N-vector representing that spectrum. In some cases the equivalent term "spectral vector" is used.

Another term, a "normalized spectrum" (or spectra in plural) is also used herein. A normalized spectrum is calculated from the original spectrum after dividing the intensity at each value by the integrated intensity of the whole spectrum. This procedure ensures that a normalized spectrum has a total integrated intensity that equals exactly 1. By doing so, it becomes possible to compare the spectral shape of two different spectra irrespective of their intensity. In many cases, a better classifier is the shape of the spectrum, rather than its intensity. Normalized spectra are preferably employed to exclude variable intensity effects which may be attributed to irregularities associated with the examined sample, the labeling procedure, or with the measurement optics.

Furthermore, all of the mathematical procedures herein described are preferably performed following a background subtraction procedure. Background subtraction is a mathematical procedure in which a spectrum of a pixel or an average spectrum of some or all of the pixels located in the background region is subtracted from the spectrum of each of the pixels. As a result, background fluorescence signals common to all pixels are subtracted, thereby increasing the classification specificity of the signals. Furthermore, the background pixels are flow characterized by spectra which are close to zero intensity at all wavelengths, which pixels are preferably eliminated for any further consideration. Therefore, only pixels associated with chromosomes are taken into further consideration.

2. Identification of External Basic Spectral Vectors:

The term "basic" as used herein in conjunction with other terms such as spectra, pixel, chromosome, cluster, class, etc., in most cases, refers to a situation wherein a single fluorophore is involved, as opposed to a combination of fluorophores. Since five fluorophores are used in the Examples herein given, there are five classes of basics, each class is associated with a different fluorophore. However, it will be appreciated that for some applications a basic feature (e.g., chromosome, pixel, class, etc.) may refer to a feature wherein more than one fluorophores are involved. In the present examples basic features refer to those associated with a single fluorophore, nevertheless, doing so, there is no intention to limit the scope of the present invention to such cases. Thus, linear decomposition, as described hereinabove and further described and exemplified below may be executed using basic pixels which form basic classes belonging to basic chromosomes which are painted by more than a single fluorophore.

As shown in Tables 1 and 2 of Example 1 above, the basic five chromosomes in the given example are chromosome numbers 2, 8, 14, 17 and 20, which are labeled with Cy5.5 (e), spectrum green (d), Texas-red (b), Cy5™ (c) and spectrum orange (a), respectively.

Hence, basic pixels are those presenting genetic material labeled with a single fluorophore, in this case genetic material derived from the above specified chromosomes. There are therefore five classes of basic pixels.

Basic spectral vectors, as referred herein, are spectral vectors of pixels in which the genetic material is labeled (e.g., painted) by a single fluorophore. In the present example, therefore, there are five classes of basic spectral vectors. In the present Example, these are spectral vectors of pixels which represent genetic material derived from the above specified five chromosomes.

External basic spectral vectors are basic spectral vectors derived from a reference preclassified color (spectral) karyotype, typically of a normal male.

The external basic spectral vectors are used according to the method of present invention to find internal basic spectral vectors of a karyotype presently classified, which are thereafter used for improved chromosome classification according to the method of the present invention. According to another embodiment of the invention, as is further described below, internal basic reference vectors are derived directly from the studied karyotype.

According to the present invention, there are few approaches for identifying the external basic spectral vectors.

Figure 3A:
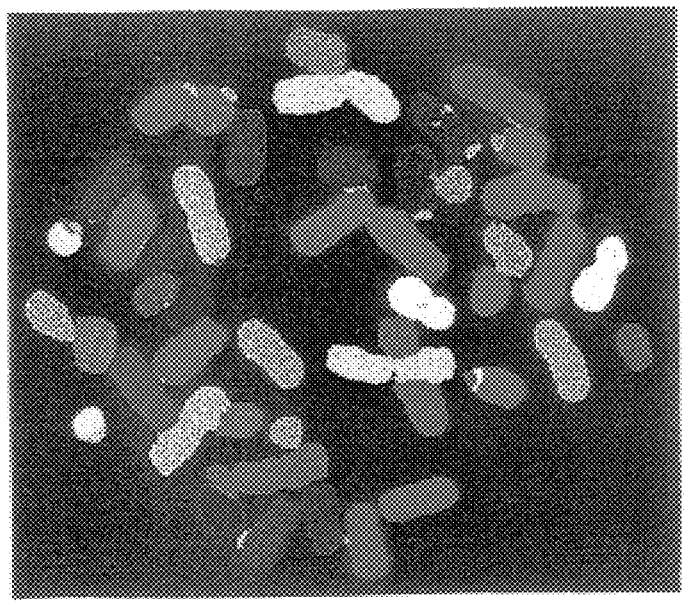
FIG. 3a presents chromosomes classified using artificial colors according to the prior art classification method described in U.S. Pat. No. 5,817,462, and in Science magazine [E. Schroeck et al. (1996). Multicolor spectral karyotyping of human chromosomes. Science, 273, 494–497.
Figure 3B:
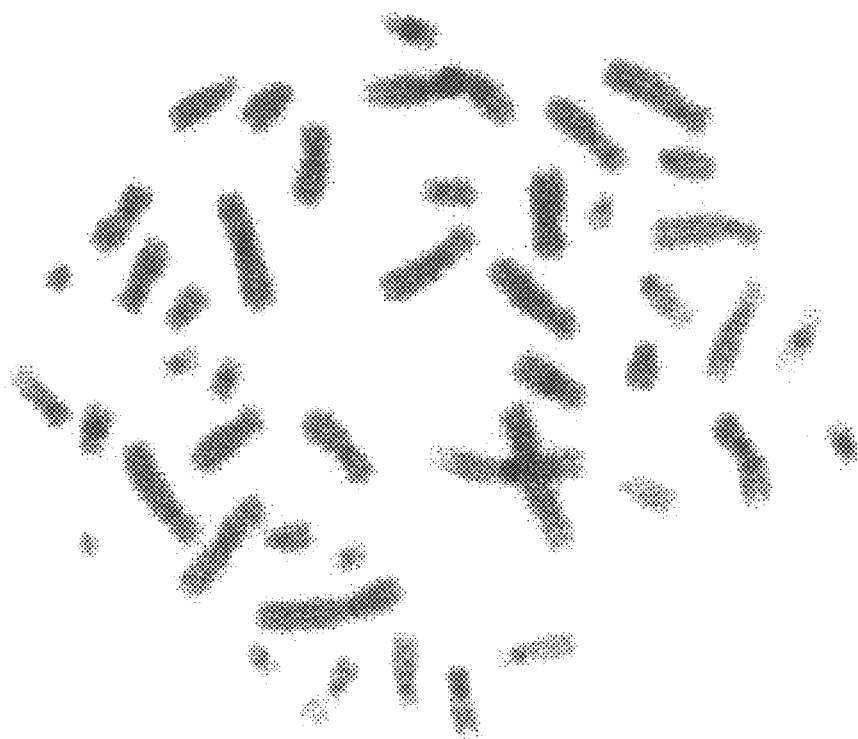
FIG. 3b presents the chromosomes of FIG. 3a R-banded with DAPI.
Figure 3C:
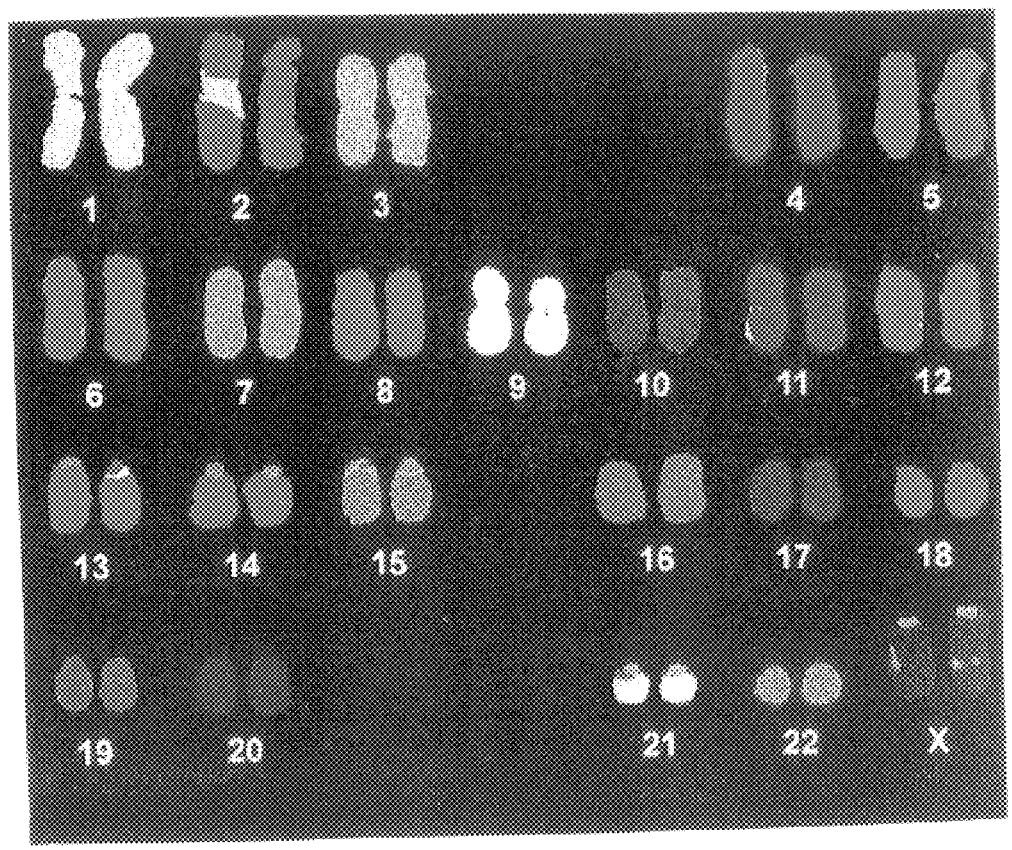

The first approach is herein described with reference to FIGS. 3a–c which present a normal color karyotype of a human male, derived using the prior art method for chromosome classification described in U.S. Pat. No. 5,817,462, and in Science magazine [E. Schroeck et al. (1996) Multicolor spectral karyotyping of human chromosomes. Science, 273, 494–497], both are incorporated by reference as if fully set forth herein. The exact types and combinations of fluorophores employed are listed in Tables 1 and 2 under Example 1 above.

The karyotype of FIGS. 3a–c was obtained as follows. First, the chromosomes were hybridized with chromosome paints labeled as described in Tables 1 and 2 above and with DAPI for R-banding. Second, chromosomes of the karyotype, shown in FIG. 3b, were identified by the conventional chromosome R-banding technique. Third, the averaged normalized spectra characterizing pixels attributed to any of the 24 chromosome types (i.e., 1–22, X and Y), as was determined by chromosome R-banding, were calculated and the resulting 24 averaged normalized spectra were used to form a library of reference spectra. Fourth, the reference spectra were used for classification of the pixels of that karyotype, the result of which classification is shown in FIG. 3a. As shown in FIG. 3c, the chromosomes were thereafter arranged in sequence as known in the art.

For classification, the normalized spectrum of each pixel in the image was compared with every one of the 24 different reference spectra of the reference library, and the similarity (e.g., minimal difference as deduced for example by a minimal square error procedure) thereof to any of the reference spectra was determined. Each pixel was then attributed an artificial predetermined distinguishing color according to its classification. The result is a color karyotype in which each of the chromosomes is colored in a different artificial color (collectively 24 different colors).

As mentioned, classification takes several spectra as reference spectra, and paints each pixel of a displayed image with a different predetermined artificial color, according to its classification, as being most similar to one of the several reference spectra.

Various algorithms are known to be prominent in classification, for Example consider Equations (3–6), $$G^{(1)}_{x,y} = \frac{I^2_{max}}{40((1/n\sum_\lambda (I_{xy}(\lambda) - R_\lambda)^2)^{1/2} + I_{max}/40)} \quad (3)$$

$$G^{(2)}_{x,y} = \frac{I^2_{max}}{20((1/n\sum_\lambda (I_{xy}(\lambda) - R_\lambda)^2)^{1/2} + I_{max}/20)} \quad (4)$$

$$G^{(3)}_{x,y} = \frac{I^2_{max}}{40(R_{max}/S_{max}(1/n(I_{xy}(\lambda) - R_\lambda)^2)^{1/2} + I_{max}/40)} \quad (5)$$

$$G^{(4)}_{x,y} = \frac{I^2_{max}}{40(R_{max}/T_{max}(1/n(\langle I_{xy}(l)\rangle - R_l)^2)^{1/2} + I_{max}/40)} \quad (6)$$

where $I_{max}$ is the maximum intensity of the image, $G_{x,y}$ is the brightness with which a pixel (of coordinates x and y) is displayed on the screen, $I_{x,y}(\lambda)$ is its spectrum, $\langle I_{xy}(\lambda)\rangle$ is the average of $I_{xy}(\lambda)$ over the group of 3×3 neighboring pixels, $S_{max}$ is the peak intensity of $I_{xy}(\lambda)$, $T_{max}$ is the peak intensity of $\langle I_{xy}(\lambda)\rangle$, $R_\lambda$ is the reference spectrum with respect to which the similarity map is calculated, $R_{max}$ is the peak intensity of the reference spectrum $R_\lambda$, and n is the number of wavelengths of the measurement.

Alternatively, Equation 7 below, may be employed to describe the degree of similarity:

$$S_{x,y} = \sqrt{\sum_{i=1}^{N} (I_{x,y}(\lambda_i) - I_R(\lambda_i))^2} \quad (7)$$

Where $I_{x,y}(\lambda)$ is the normalized spectrum of pixel x,y, $I_R(\lambda)$ is the normalized reference spectrum and N is the number of wavelengths. In this equation, S decreases when the similarity between the spectra increases, and vice versa. In the extreme case, when the spectra are identical, S becomes equal to zero.

When performing this calculation with k different reference spectra, one obtains k different values of S for each pixel, i.e., $S_1 S_2, \ldots S_k$. The smallest of those shows which of the reference spectra is the most similar to the pixel's spectra. Yet, as will be appreciated by one ordinarily skilled in the art, other equations that reflects the similarity are also known and applicable. Thus, classification may also be performed using a simple minimal square error distance algorithm or a complicated principal component analysis.

Using this approach, one can identify the external basic spectral vectors, five in the present example. It should be noted that any of the external basic spectral vectors may be of any specific basic pixel presenting that basic spectral vector, or preferably the average of spectral vectors of two or more basic pixels of a single basic pixel's class.

Nevertheless, it should be noted that such identification is based upon first identifying the chromosomes using a conventional banding technique (DAPI for R banding in the present case). Therefore, this approach is less favorable.

However, if a universal experimental protocol is maintained, the identification of the external reference spectral vectors has to be performed once for all further chromosome classifications, as herein described with respect to some embodiments of the method of the present invention.

Figure 4A:
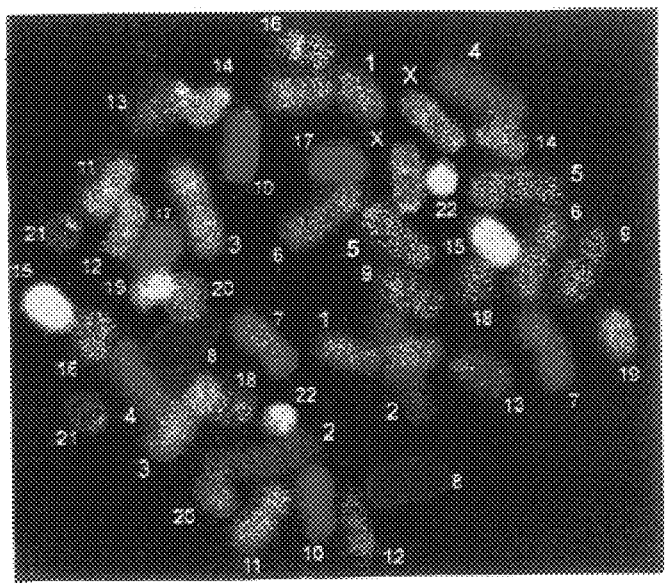
FIG. 4a–b presents the chromosomes of FIGS. 3a–c, now classified using an RGB algorithm according to the prior art method described in U.S. Pat. No. 5,817,462, and in Science magazine [E. Schroeck et al. (1996) Multicolor spectral karyotyping of human chromosomes. Science, 273, 494–497, as a spread and as a karyotype.
Figure 4B:
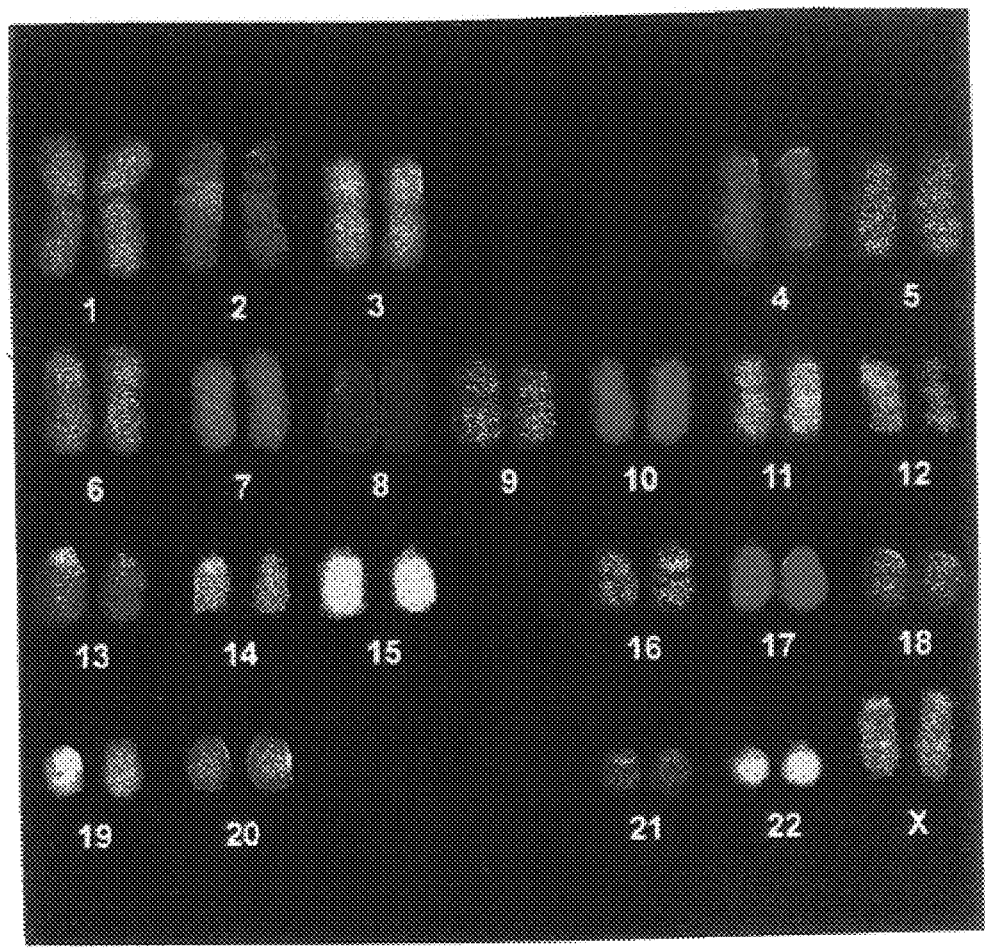

The second approach is herein described with reference to FIGS. 4a–b, which present a normal color karyotype of the same human male, derived using another prior art method for chromosome classification described in U.S. Pat. No. 5,817,462, and in Science magazine [E. Schroeck et al. (1996) Multicolor spectral karyotyping of human chromosomes. Science, 273, 494–497]. The exact types and combinations of fluorophores employed are listed in Tables 1 and 2 under Example 1 above.

According to the second approach an RGB algorithm which integrates the optical signal over the spectral range (e.g., 400 nm to 760 nm) of the CCD array was used to obtain an RGB image of the chromosomes, in which each pixel is attributed a combination of red, green and blue intensities according to three weighting functions, $\{w_r(\lambda), w_g(\lambda), w_b(\lambda)\}$, which correspond to the tristimulus response functions for red (R), green (G) and blue (B).

FIG. 5 presents an example of the power of this simple algorithm. Consider choosing $\{w_r, w_g, w_b\}$ to be Gaussian or other functions distributed "inside" a spectrum of interest, the resulting pseudo-color image that is displayed in this case emphasizes only data in the spectral regions corresponding to the weighting functions, enabling spectral differences in these three regions to be detected more clearly.

Figure 6:
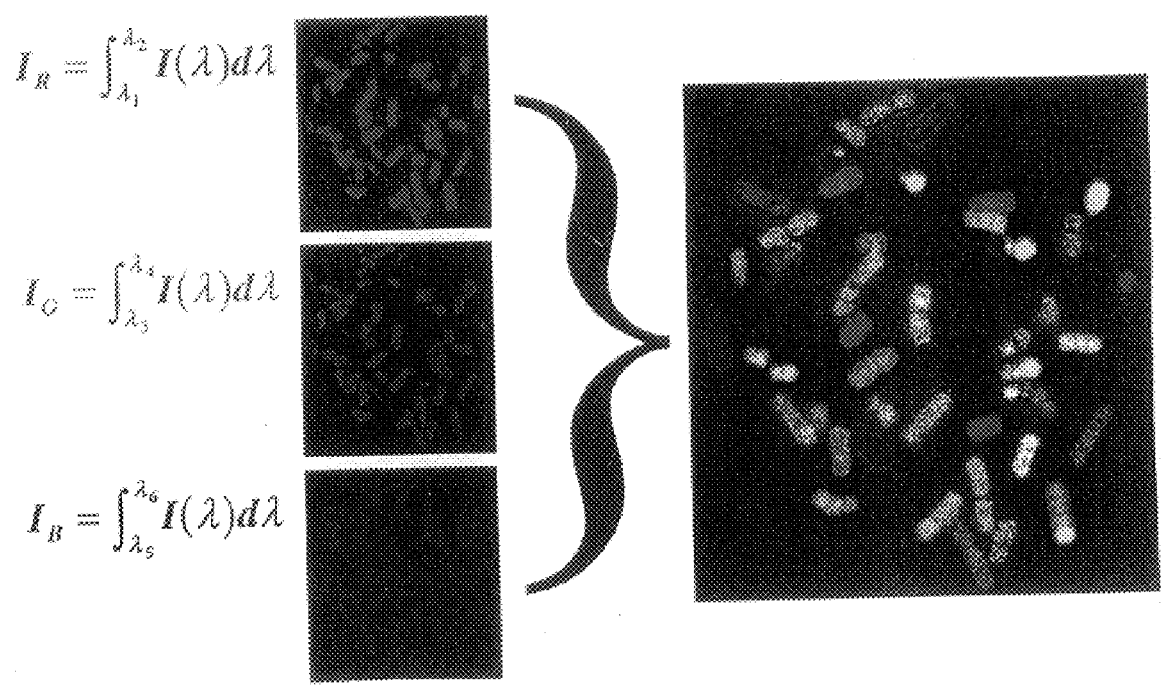
FIG. 6 presents the steps in integrating RGB images for chromosome classification, wherein $w_r$, $w_g$, $w_b$ are simple square weighting functions.

FIG. 6 presents the power of the RGB algorithm for chromosome classification. In this case $w_r$, $w_g$, $w_b$ are simple square weighting functions, wherein for $w_r$(red) $\lambda_1$=640 nm and $\lambda_2$=750 nm; for $w_g$(green) $\lambda_1$=555 nm and $\lambda_2$=640 nm; and for $w_b$(blue) $\lambda_1$=450 nm and $\lambda_2$=555 nm. The simple weighting functions $w_r$, $w_g$, $w_b$ are integrated to generate an RGB image of the chromosomes, shown on the right.

Under predetermined experimental conditions and predefined weighting functions for the RGB colors, the basic chromosomes and the basic pixels can be distinguished, as well as most or all of the other chromosomes. In particular, the experimental conditions, i.e., types and combinations of fluorophores, and the RGB weighting functions are selected such that basic pixels are attributed unique colors (i.e., basic colors) which clearly distinguish them from one another and from all other (19 in this case) "non-basic" chromosomes/pixels. Table 4 summarizes the association of fluorophores, basic chromosomes and basic colors selected for the present example.

TABLE 4

| Symbol | Fluorophore | Basic Chromosome | Basic Color |
|---|---|---|---|
| a | Spectrum Orange | 20 | Green |
| b | Texas-Red | 14 | Yellowish-Green |
| c | Cy5™[1] | 17 | Red |
| d | Spectrum Green | 8 | Blue |
| e | Cy5.5™[1] | 2 | Reddish-Brown |

[1]from Amersham

Figure 7:
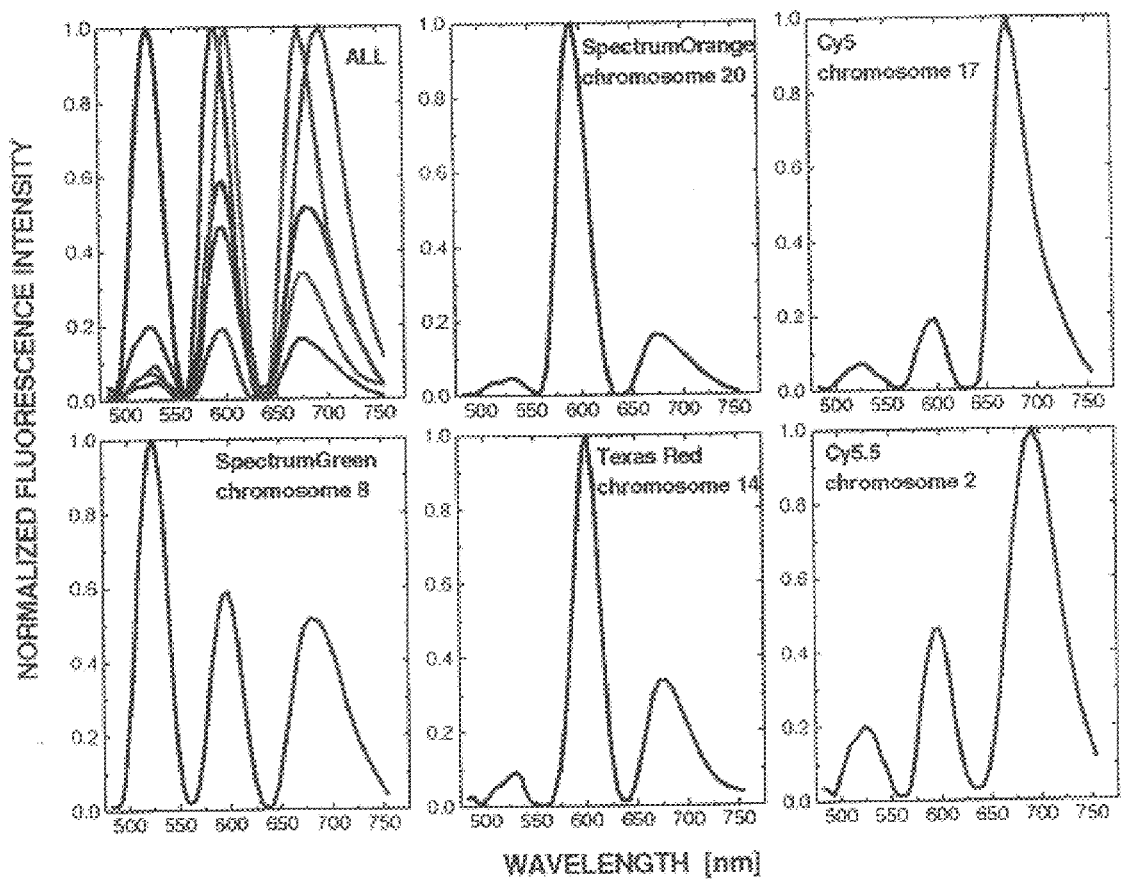
FIG. 7 presents the five basic external spectra derived using the exemplified experimental procedure, wherein the fluorophores and basic chromosomes are specified.
Figure 8A:
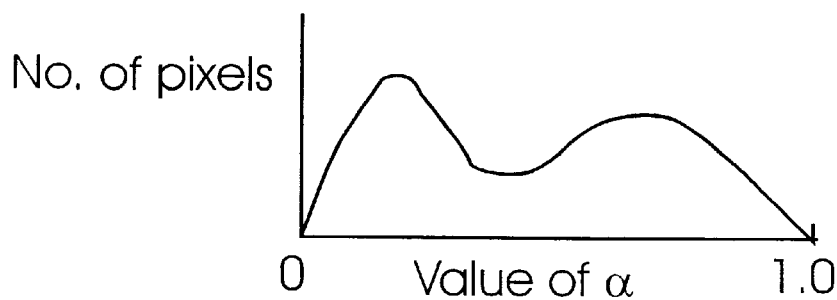
FIGS. 8a–e present plots representing the number of pixels having any value (0–1.0) of the decomposition coefficients $\alpha$-$\epsilon$, respectively.
Figure 8B:
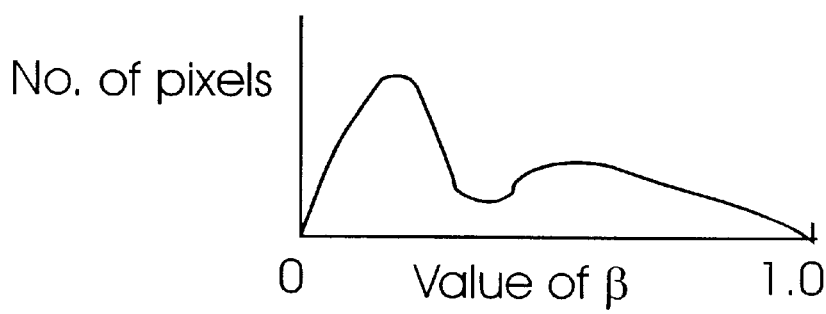
Figure 8C:
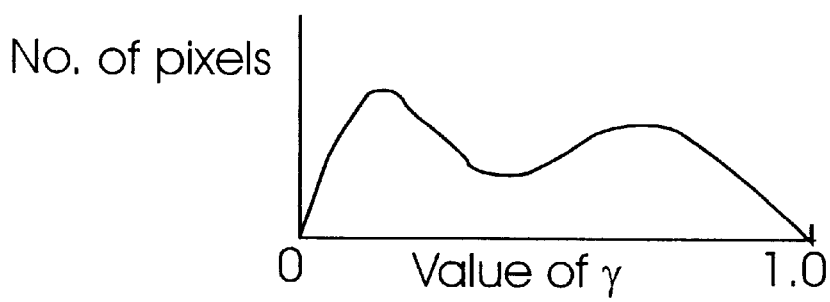
Figure 8D:
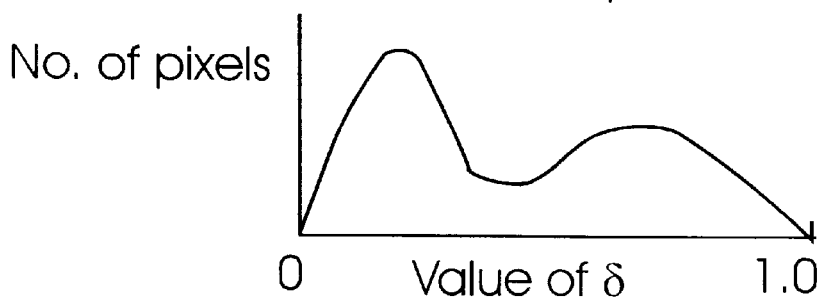
Figure 8E:
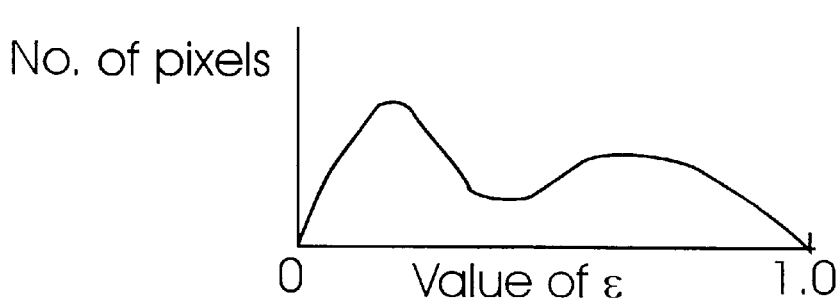

FIG. 7 presents the five basic external spectra derived using the exemplified experimental procedure, wherein the fluorophores and basic chromosomes are specified.

Using the RGB approach for identification of the external basic spectral vectors has an advantage over the classification approach hereinabove described, since no prior identification of the chromosomes by conventional banding techniques (e.g., R-banding) is required, where it is required to generate the external reference library according to the above described classification approach. This is the case since the exact experimental procedure (e.g., the procedure of Tables 1 and 2 above), and the given weighting functions and the pre-selected three color output (e.g., RGB), can be selected such that each of the pixels having a basic spectral vectors, will be colored highly distinctively. In fact, as is further detailed hereinbelow, using the RGB approach may be used directly to find internal basic spectral vectors, which are thereafter used to find all other reference spectra for classification.

3. Identification of Internal Basic Spectral Vectors:

Using the external basic spectral vectors, a procedure of identifying the internal basic spectral vectors is initiated. To this end, according to the present invention, a linear decomposition algorithm is executed.

In the present example, linear decomposition is performed using the five external basic spectral vectors, herein defined as A, B, C, D and E, to obtain a decomposition K-vector (a decomposition 5-vector in the present example) of decomposition coefficients for each pixel in the image.

Hence, during this mathematical procedure, for each pixel in the image, a set of five decomposition coefficients α, β, γ, δ and ε, respectively, is calculated. The α–ε coefficients are selected such that multiplying each of the A–E basic external spectral vectors in its corresponding coefficient, and summing the multiplication result spectral vectors, results in a spectrum (a spectral vector) which is substantially identical to that pixel's spectrum. Therefore, each of the pixels in the image may be represented as a decomposition-K-vector, a decomposition-5-vector, composed of the α–ε decomposition coefficients in the present example. Of the decomposition-5-vectors thus calculated, internal basic pixels are by definition represented by basic decomposition-5-vectors. These vectors are herein defined as external basic decomposition-K-vectors, since they are defined using K external basic spectral vectors.

This can be described mathematically for any number of required decomposition coefficients. Let $C_j$ be the coefficient vectors, wherein J=1 . . . k (k equals 5 in the present example), then:

$$I(\lambda_i) = \sum_{j=1}^{K} C_j \cdot I_j(\lambda_i) \tag{8}$$

where $I(\lambda_i)$ is the spectrum of a certain pixel; and $I_j(\lambda_i)$ are the vectors.

In practice, due to noise, it might not be possible to obtain a set of coefficients that exactly matches the above equation, and a small residual must therefore be added. Due to the quality of the results and the high signal to noise ratio obtainable with the SpectraCube™ system, this residual is relatively small.

According to the method of the present invention, the linear decomposition coefficients α–ε are used to identify internal basic pixels which, by definition, have internal basic spectral vectors, which are herein defined as A'–E', respectively.

With reference now to FIGS. 8a–e, presented are plots representing the number of pixels having any value (0–1.0) of the decomposition coefficients α–ε, respectively.

As shown in FIGS. 8a–e, for each of the α–ε decomposition coefficients, the plot is characterized by two peaks separated therebetween by a valley. The first peak represents pixels having low decomposition coefficient values (e.g., 0–0.3), whereas the second peak represents pixels having high decomposition coefficient values (e.g., 0.3–1.0). Pixels represented in the second peak of any of the decomposition coefficients (α–ε) have high probability to include the fluorophore associated with that coefficient.

As shown in Table 5, below, based on fluorophore composition (a–e), one can define a basic binary-K-vector, a basic binary-5-vector in the present example, for each of the internal basic spectral vectors A'–E'. Using the defined basic binary 5-vectors and a high cut off value, e.g., about 0.75, for transforming any of the five basic decomposition 5-vectors to a basic binary 5-vector, one can select basic pixels having the internal basic spectral vectors A'–E'.

TABLE 5

|    | a | b | c | d | e |
|----|---|---|---|---|---|
| A' | 1 | 0 | 0 | 0 | 0 |
| B' | 0 | 1 | 0 | 0 | 0 |
| C' | 0 | 0 | 1 | 0 | 0 |
| D' | 0 | 0 | 0 | 1 | 0 |
| E' | 0 | 0 | 0 | 0 | 1 |

Due to the high cut off values selected, the probability of properly selecting internal basic pixels having internal basic spectral vectors, is exceedingly high.

After finding the basic pixels having internal basic spectral vectors (A'–E'), internal reference basic spectral vectors may be calculated by, for example, separately averaging the basic spectral vectors of basic pixels belonging to each basic class. Alternatively, the internal basic spectral vectors of selected pixels (5 in this case, one for each basic class) may be directly employed as the internal reference basic spectral vectors.

In any case, the internal reference basic spectral vectors thus defined are used according to the method of the present invention to calculate internal decomposition-K-vectors (e.g., 5-vectors) for each of the pixels in the image, similar to as is described hereinabove with respect to the external basic spectral vectors.

Following is the mathematical description of the linear decomposition algorithm. Practically, the coefficients of the linear decomposition algorithms are calculated as follows.

Assume that $I(\lambda_i)$ is the spectrum of a certain pixel and that i is an index of the wavelength index, i=1 . . . N, where N is the total number of wavelengths in the spectrum, and that a set of K basic reference spectra is given, $I_j(\lambda_i)$ j=1 . . . K. The search is for a set of K coefficients, $C_j$ so that:

$$I(\lambda_i) = \sum_{j=1}^{K} C_j \cdot I_j(\lambda_i) + \varepsilon(\lambda_i) \tag{9}$$

with $\varepsilon(\lambda_i)$ being the smallest possible error.

It is important to note that Equation 9 should hold for each one of the N wavelengths $\lambda_i$. This equation can also be written as:

$$\varepsilon(\lambda_i)^2 = \left( I(\lambda_i) - \sum_{j=1}^{K} C_j \cdot I_j(\lambda_i) \right)^2 \tag{10}$$

or by summing over all the N wavelengths, $$\sum_{i=1}^{N} \varepsilon^2(\lambda_i) = \sum_{i=1}^{N} \left( I(\lambda_i) - \sum_{j=1}^{K} C_j \cdot I_j(\lambda_i) \right)^2 \tag{11}$$

Now, because the square of the residual is always positive, one is looking for the set $C_j$ so that $$\sum_{i=1}^{N} \varepsilon^2(\lambda_i)$$

is minimized. This solution can be found by taking the partial derivative of the right side of Equation 11 relative to each one of the components $C_j$, and set the value to zero. This results in a set of K equations having K unknowns, $C_j$. Those equations can be written in a format of a matrix 25 calculation. The derivative $\partial/\partial C_m$ of the right side of Equation 11 yields:

$$2\sum_{i=1}^{N}\left[\left(I(\lambda_i)-\sum_{j=1}^{K}C_j I_j(\lambda_i)\right)\cdot I_m(\lambda_i)\right] \quad (12)$$

Equation 12 is set equal zero, and after a different arrangement, yields:

$$\sum_{i=1}^{N}\left[\sum_{j=1}^{K}C_j I_j(\lambda_i)\cdot I_m(\lambda_i)\right]=\sum_{i=1}^{N}I(\lambda_i)\cdot I_m(\lambda_i) \quad (13)$$

Equation 13 can now be written in a matrix format (14):

$$\begin{bmatrix}\sum_{i=1}^{N}I_1^2(\lambda_i) & \sum_{i=1}^{N}I_2(\lambda_i)\cdot I_1(\lambda_i) & \cdots & \sum_{i=1}^{N}I_K(\lambda_i)\cdot I_1(\lambda_i) \\ \sum_{i=1}^{N}I_1(\lambda_i)\cdot I_2(\lambda_i) & \sum_{i=1}^{N}I_2^2(\lambda_i) & \cdots & \sum_{i=1}^{N}I_K(\lambda_i)\cdot I_2(\lambda_i) \\ \vdots & & \ddots & \\ \sum_{i=1}^{N}I_1(\lambda_i)\cdot I_K(\lambda_i) & \sum_{i=1}^{N}I_2(\lambda_i)\cdot I_K(\lambda_i) & \cdots & \sum_{i=1}^{N}I_K^2(\lambda_i)\end{bmatrix}\cdot\begin{bmatrix}C_1 \\ C_2 \\ \vdots \\ C_K\end{bmatrix}=\begin{bmatrix}\sum_{i=1}^{N}I_1^2(\lambda_i) \\ \sum_{i=1}^{N}I_1(\lambda_i)\cdot I_2(\lambda_i) \\ \vdots \\ \sum_{i=1}^{N}I_1(\lambda_i)\cdot I_K(\lambda_i)\end{bmatrix}$$

One can write Equation 14 as $\tilde{A}\cdot C=V$, wherein $\tilde{A}$ is a symmetric matrix and all its elements can be directly calculated. By finding the reciprocal matrix $\tilde{A}^{-1}$ and multiplying from left, one gets:

$$C=\tilde{A}^{-1}\cdot V \quad (15)$$

The components $C_j$ are therefore found.

4. Identification of all Internal Reference Spectral Vectors:

As mentioned above, the K, say 5, internal basic spectral vectors may serve as reference spectral vectors for the classification of pixels presenting genetic material labeled solely by any single fluorophore a–e, respectively. Nevertheless, for full classification additional reference spectral vectors, which represent the combinations of the a–e fluorophores used for hybridization (see Table 2) are further required.

The K internal basic spectral vectors, according to the present invention, are, therefore, used for identifying pixels having any of the additional required (19 in this case) internal reference spectral vectors.

To this end, as shown in Table 6, first, each required reference spectral vector is defined as a binary 5-vector, according to the fluorophores associated with it. Remember, the basic binary vectors were already defined in Table 4 above.

TABLE 6

| Chr. No. | Chr. paint | Fluorophores | binary vector | | | | |
|---|---|---|---|---|---|---|---|
| | | | a | b | c | d | e |
| 1 | 1 | b, c, d | 0 | 1 | 1 | 1 | 0 |
| 2 | 2 | e | 0 | 0 | 0 | 0 | 1 |
| 3 | 3 | a, c, d, e | 1 | 0 | 1 | 1 | 1 |
| 4 | 4 | c, d | 0 | 0 | 1 | 1 | 0 |
| 5 | 5 | a, b, d, e | 1 | 1 | 0 | 1 | 1 |
| 6 | 6 | b, c, d, e | 0 | 1 | 1 | 1 | 1 |
| 7 | 7 | b, c | 0 | 1 | 1 | 0 | 0 |
| 8 | 8 | d | 0 | 0 | 0 | 1 | 0 |
| 9 | 9 | a, d, e | 1 | 0 | 0 | 1 | 1 |

TABLE 6-continued

| Chr. No. | Chr. paint | Fluorophores | binary vector | | | | |
|---|---|---|---|---|---|---|---|
| | | | a | b | c | d | e |
| 10 | 10 | c, e | 0 | 0 | 1 | 0 | 1 |
| 11 | 11 | a, c, d | 1 | 0 | 1 | 1 | 0 |
| 12 | 12 | b, e | 0 | 1 | 0 | 0 | 1 |
| 13 | 13 | a, e | 1 | 0 | 0 | 0 | 1 |
| 14 | 14 | b | 0 | 1 | 0 | 0 | 0 |
| 15 | 15 | a, b, c | 1 | 1 | 1 | 0 | 0 |
| 16 | 16 | b, d | 0 | 1 | 0 | 1 | 0 |

TABLE 6-continued

| Chr. No. | Chr. paint | Fluorophores | binary vector | | | | |
|---|---|---|---|---|---|---|---|
| | | | a | b | c | d | e |
| 17 | 17 | c | 0 | 0 | 1 | 0 | 0 |
| 18 | 18 | a, b, d | 1 | 1 | 0 | 1 | 0 |
| 19 | 19 | a, c | 1 | 0 | 1 | 0 | 0 |
| 20 | 20 | a | 1 | 0 | 0 | 0 | 0 |
| 21 | 21 | d, e | 0 | 0 | 0 | 1 | 1 |
| 22 | 22 | b, c, e | 0 | 1 | 1 | 0 | 1 |
| X | X | a, e | 1 | 0 | 0 | 0 | 1 |
| Y | Y | c, d, e | 0 | 0 | 1 | 1 | 1 |

Thereafter, using the abundance plots of FIGS. 8a–e and a second, lower, threshold value (e.g., about 0.3) or preferably a threshold range (e.g., about 0.25–0.35), which is preferably positioned substantially at the valley between the first and second peaks of the plots, each of the new decomposition-K-vectors of each of the pixels is transformed into a transformed binary-K-vector. In the present example expected are 24 types of transformed binary-5-vectors for male karyotypes and 23 for female karyotypes. In cases where a threshold range is used, some binary-5-vectors thus obtained lack one or more binary components (0 or 1) for one or more of the decomposition coefficients. This is the case since values within the threshold range are not classified into a binary term (0 or 1).

For presentation of a color karyotype, pixels having identical transformed binary-K-vectors are attributed an identifying artificial color (24 different colors for males, 23 for females), according to a predetermined pattern associated with the defined binary vectors of Table 6 above.

Alternatively, the spectral vectors of some or all of the pixels having identical transformed binary-K-vectors are averaged to yield 24 (or 23 for female) internal reference spectral vectors, which are thereafter used for classification, for example, as described above with respect to Equations 3–7, or other suitable classification procedure (e.g., minimal square error, principal component analysis, etc.), wherein a pixel's spectrum is classified to a class according to its highest resemblance to any of the reference spectral vectors employed for classification.

Alternatively, the decomposition-K-vectors of some or all of the pixels having identical transformed binary-K-vectors are averaged to yield L (24 for human male 23 for female) internal reference vectors, which are thereafter used for classification as described above with respect to Equations 3–7, or other suitable classification procedure (e.g., minimal square error), wherein a pixel's decomposition-K-vector is classified to a class according to its highest resemblance to any of the L internal reference vectors employed for classification.

Figure 9A:
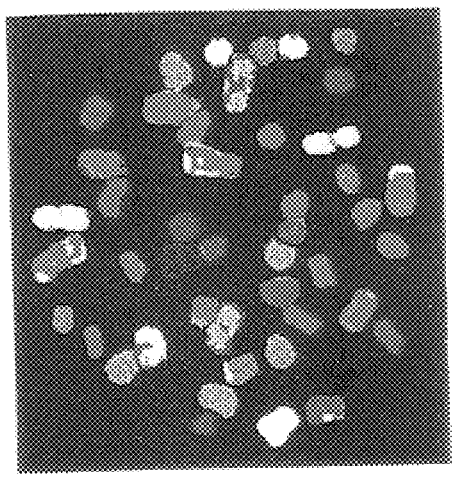
FIGS. 9a–c present chromosomes of a normal male classified according to the method of the present invention; chromosomes of the same male shown in RGB; and a combined karyotype, respectively.
Figure 9B:
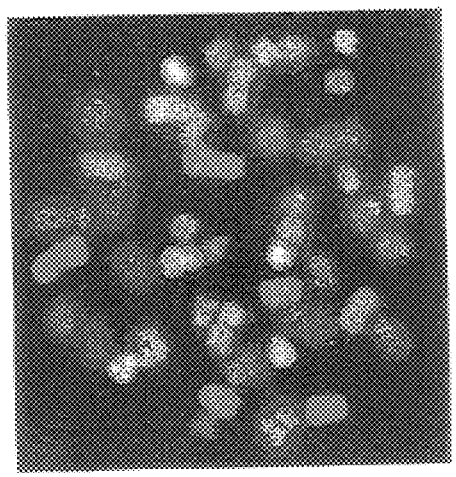

With reference now to FIG. 9a, presented is a normal male chromosome spread classified as herein above described. FIG. 9b present the same spread in RGB, as described with respect to FIGS. 4a–b above. Whereas, FIG. 9c, presents a side by side combined color karyotype of the chromosomes of FIGS. 9a and 9b, wherein classified chromosomes are shown on the left and RGB chromosomes, on the right.

Figure 9C:
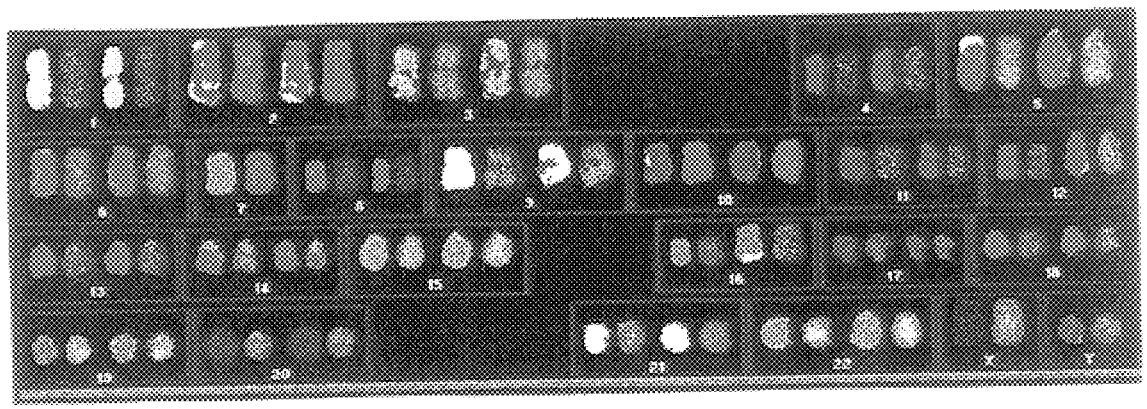

Carefully examining FIGS. 9a and 9c, one notes that some of the pixels associated with chromosomes are misclassified, some others are unclassified, yet cannot be seen over the background, as these are attributed a black color. The reason is that some of the pixels are not classified into any of the classes, i.e., into any of the 24 types of binary-5-vectors (theoretically there are additional 8 such vectors), whereas other pixels are misclassified to the wrong class. In some cases, some of the 24 types of binary-5-vectors were associated with a very small number of pixels, suggesting an artifact (not shown).

The following further demonstrates this problem. A pixel-binary-5-vector association table is calculated. Each of the pixels (1,1 through x,y) is associated with one of the 24 binary-5-vectors (see Table 5). Then, the total number of pixels associated with any of the 1 through 24 binary-5-vectors is counted. Some vectors will then have very few associated pixels. Some pixels will not be associated with any of the 1 through 24 binary-5-vectors. Both cases are artifacts, which are due to the arbitrary selection of the second range threshold, as described above.

4. Spectral-Spatial Based Autosegmentation:

At this point, all of the spectral information was already exploited for classification. However, no use was so far done with the spatial information. One should keep in mind that the distribution of pixels carries classification information since adjacent or close pixels have a higher probability of belonging to a cluster of pixels presenting genetic material derived from a particular chromosome or part thereof, and therefore, theoretically, they should be similarly classified. Furthermore, each cell is characterized by a given number of chromosomes, each having a characterizing appearance in terms of, for example size (e.g., length), and relative location of its centromere.

Typically, the number of clusters for a well spread (no overlapping chromosomes present) normal human karyotype is 46 (one for each chromosome). These clusters are divided into 24 classes for males and 23 for females. When translocations occur, the total number of clusters increases. In cancerous cells, especially if grown for many generations in culture, the number of clusters due to translocations may reach a hundred or more.

Recall that each of the pixels in the image is represented by a decomposition-K-vector (obtained either using external or preferably internal basic spectral vectors and the second cut off value as described above). Therefore, a clustering procedure may be initiated.

To this end, variations among the decomposition-K-vectors of adjacent pixels are monitored. These variations are used for clustering. For example, when the K-vectors variation (e.g., as is determined, for example, by minimal square error) between any two adjacent pixels is below a predetermined threshold, they are clustered into a cluster, whereas, when the variation between any two adjacent pixels exceeds the predetermined threshold, they are considered as belonging to different clusters. The result of the clustering procedure is the generation of clusters of pixels having similar decomposition-K-vectors. Similarly, clustering may be effected using the normalized spectral vectors of the pixels. In fact, clustering is a type of classification.

Using a third threshold value, each of the identified clusters may be transformed into a transformed binary-K-vector and thereby be associated with one of the 24 defined binary-K-vectors of Table 5. In other words, if the relative number of pixels of a given cluster associated with one of the 24 defined binary K-vectors is above the third threshold (e.g., above about 80%), then that cluster is associated with that vector. Optimally, a normal karyotype should have 46 clusters associated with 24 (male) or 23 (female) types of binary K-vectors. Thus, for a male, each of the 1 through 22 binary-K-vectors is expected to be associated with two clusters, whereas the 23rd and 24th binary-K-vectors are expected to be associated with clusters of genetic material derived from chromosomes X and Y, respectively.

Further according to the method of the present invention, to obtain internal reference vectors for classification, the spectra or the decomposition-K-vectors of some or all of the pixels of clusters associated with each specific binary-K-vector are averaged.

These 23 or 24 averaged vectors are highly suitable for classification of the presently analyzed image, since they are derived from pixels within the image itself, however while doing so, no need for using conventional banding chromosome classification arises.

However, in some cases, few clusters are not classified. By definition, a non-classified cluster lacks a group of pixels associated with any one of the binary-K-vectors, which is above the threshold for clusters classification. As a result, in some of these cases some binary-K-vectors have no clusters therewith associated, and some internal reference vectors for classification are, therefore, still missing.

The non-classified clusters typically include pixels which are not associated with any of the 24 defined binary-K-vectors, as they include at least one (typically one) non-classified binary component, resulting from the threshold range employed. By definition, the non-classified binary component may be either 1 or 0.

In a preferred embodiment of the invention, these two options are examined against all of the defined binary-K-vectors to which no cluster was so far associated. In most cases one of the two options matches such a vector and that pixel is thereby associated with that vector.

Following this analysis, the clustering procedure, as described above. is repeated. In most cases, following this step every single defined binary-K-vector is associated with at east one, typically two or more clusters, depending, for example, on the gender, the level of translocations and the presence or absence of overlapping chromosomes in the analyzed chromosomes spread.

Following the repeated clustering procedure the internal reference vectors or classification are recalculated. To this end the spectra or the decomposition-K-vectors of some or all of the pixels of clusters associated with any specific binary-K-vector are preferably averaged. The reference vectors thus obtained are thereafter used for classification as hereinabove described.

In rare cases, however, also after the reclustering step, one or more of the defined binary-5-vectors are still not associated with any cluster. A cluster associated with that vector may be identified using a conventional chromosome banding technique (e.g., DAPI for R-banding).

Now, for most cases, each binary 5 vector is associated with at least one cluster and therefore internal reference vectors can be calculated and classification performed.

As seen in FIG. 9a, still, in some cases after the classification some chromosomes show clusters of pixels colored in a different color. These clusters may be the result of either translocation, which is legitimate, or a classification artifact. Each of these clusters may therefore be examined. To this end, the degree of resemblance (preferably in percents) between the spectral vector or the decomposition-K-vector of each or some of the pixels within the examined cluster is monitored with respect to the relevant reference vectors employed. The best first matches (e.g., about five) are displayed, enabling the operator to differentiate between artifacts and translocations.

EXAMPLE 4

Figure 10A:
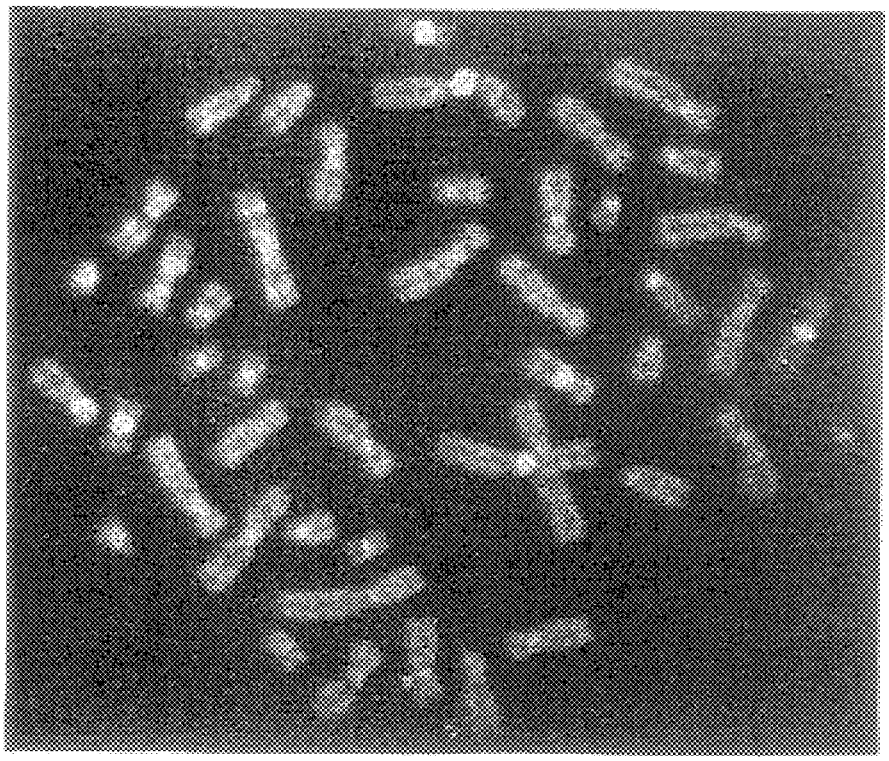
FIGS. 10a–b present an RGB chromosome spread (FIG. 10b)analyzed similar to the spread of FIG. 4a and its banded pattern resulting from conventional R-banding (DAPI), (FIG 10a)
Figure 10B:
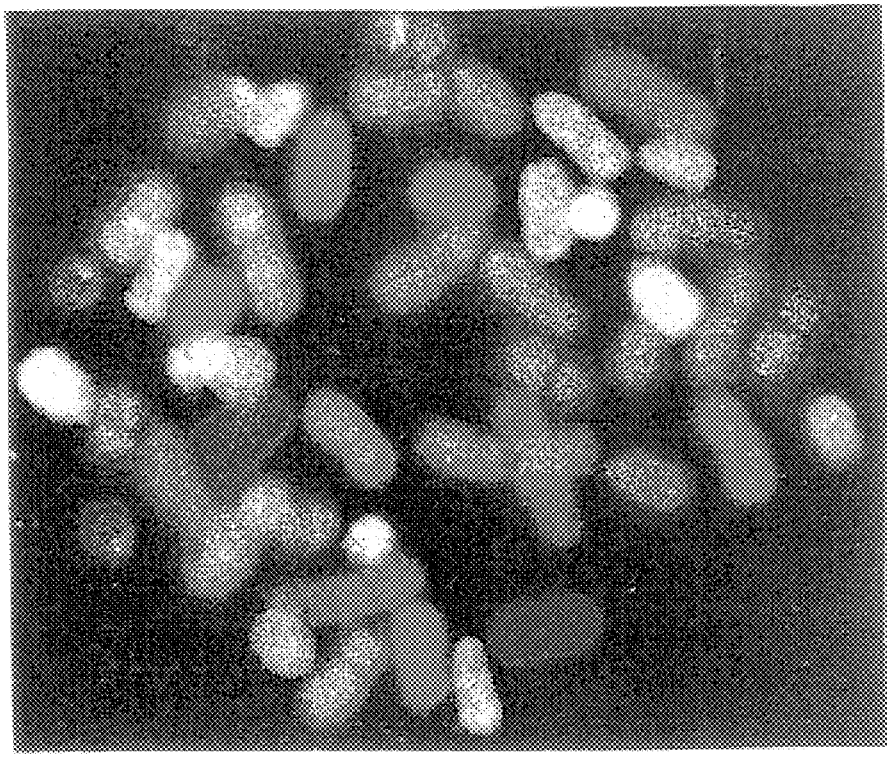

Overlay Composition of a Spectral Karyotype Image and Conventional Banding Image With reference now to FIGS. 10a–b and 11a–b. As is well established by now, two data sets may be obtained from a labeled metaphase chromosome spread, or in general, from other materials labeled with multiple dyes. One of these is a monochrome image, such as a G-band transmission image or a R-band (DAPI) fluorescence image, the later is shown as a negative image in FIG. 10a. The former is a multi-band image, such as a spectral image taken under fluorescence after labeling with chromosome specific probes, as shown in FIG. 10b.

It is current practice to display either the G-band or DAPI monochrome images after some manual and/or automatic preprocessing to normalize or enhance spatial features. These images are referred herein as banded images. These images may be constructed either as dark foreground on light background or vice versa.

Whether the multi-band image is composed of many spectral wavelength bands or fewer bands obtained using an image acquisition technology as, for example, described by Speicher et al. in Nature Genetics. 12:368–375 (1996), it is possible to create a color image to visualize those data. There are various ways in which such a color image may be constructed. In the simplest method several of the bands are assigned colors and then these layers overlaid to create a color image. Another method is to build each color layer using a function applied (for each pixel) to the full set of bands, and then to overlay the color layers. This color image may then be manually and/or automatically enhanced using image enhancement techniques. Examples for color images are the RGB images and the classification images described hereinabove. For the purposes of this description, a color image refers to any color image created using the data acquired from imaging measurement of materials labeled with multiple dyes.

In the case of a measurement of a metaphase chromosome spread labeled with multiple fluorescent dyes using an interferometer based spectral imager such as the SpectraCube™ system, one finds that there is a significant difference between the spatial character of the banded image and the color image. In the color image, as seen in FIG. 10b, the chromosomes appear thick and, in many cases, the centeromere is non detectable. This is probably due to probe molecules attached at one end to the chromosomes and loose at their other end, protruding from the general outline of the chromosomes as perceived when banded, as seen, for example in FIG. 10a.

The idea described herein is to derive a composite color-banded image using both the banded image and the color image that shows features not apparent in either image by itself. In this way one achieves a basic advantage over the display of a banded image or a color image separately: the user can have a direct and immediate impression of the chromosomes in the way the user is used to see them and analyze them for many years, and, at the same time, get the additional information provided by the color image based on spectral vector classification, not available in the banded image. The superposition can be done only by software after the images have been acquired completely, analyzed and classified, because they cannot be measured simultaneously, due to the different labeling procedure required for the banded image and for the spectral or vector based images.

Thus, the implementation described herein uses the monochrome banded image and the color image to create a composite color-banded image. The example shown below is from a chromosome metaphase, although the idea may be applied to other dye labeled materials.

Before the images can be used to form the composite, they must be subjected to spatial registration, so that one knows the correspondence between points in the two images. This was done in the present case by resizing, rotating, and shifting the color image until it matched the monochrome image. In general this correspondence may be made automatically, manually, or semi-automatically.

Figure 11A:
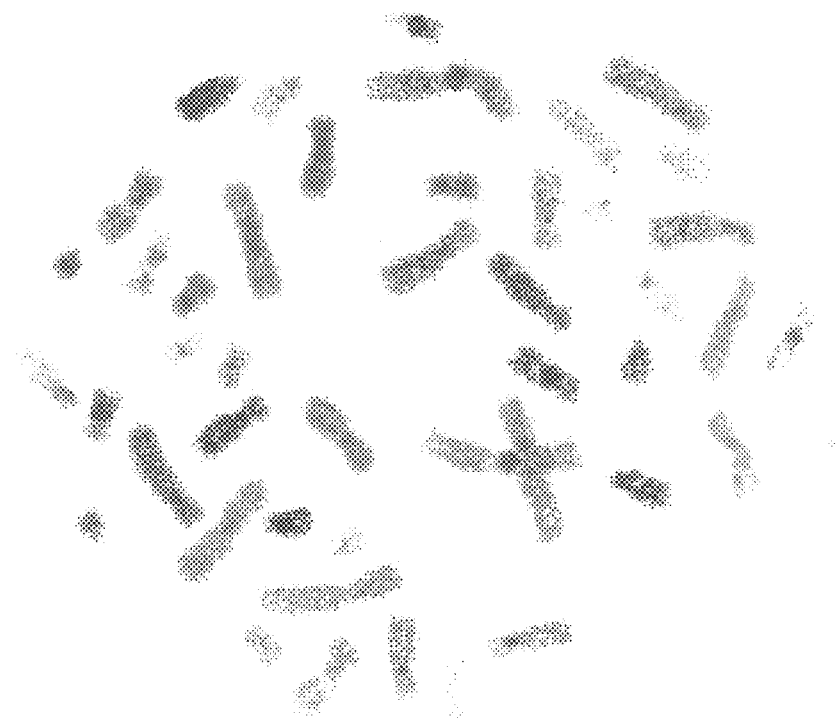
FIGS. 11a–b present two images which are overlaid composites of FIGS. 10a and 10b, according to the present invention.
Figure 11B:
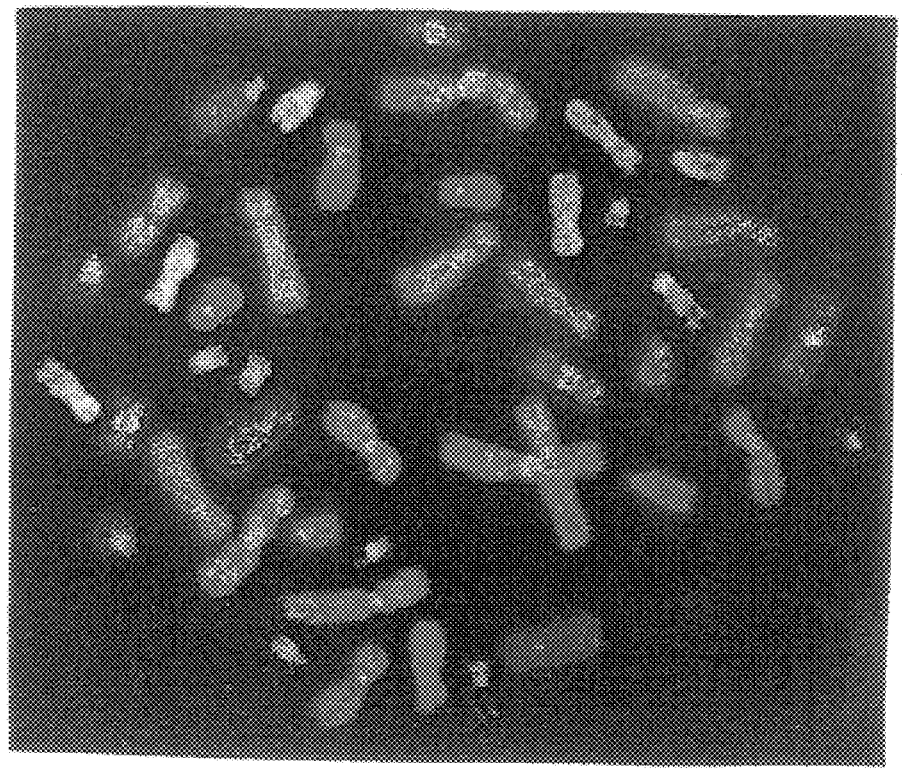

FIGS. 11a and 11b preset composite images according to the present invention. In the method used to create the composite image of FIG. 11a the luminance or intensity value is derived directly from the (white on black) DAPI banded image, and the hue is derived from the corresponding point in the color image, an RGB image in this example. The difference in the method used to create FIG. 11b was that the luminance value came from the inverse of the DAPI banded image. It is clear that any positive or negative monochrome image of banded chromosomes, which are banded according to any banding protocol, may be alternatively employed. At present DAPI banding is preferred since the fluorophores employed for chromosome painting and DAPI measurements can be performed using the same measurement device, e.g., the SpectraCube™ system.

The results provide the user with (i) chromosomes shapes with which the user is familiar; and (ii) overlaid information of spectral and conventional banding karyotyping.

Thus, this implementation uses a monochrome image and a color image and then derives a composite. A variation on this idea is to skip the creation of intermediary images, to use the initial measurements of the monochrome and multi-band data to directly construct a composite image. However, any other overlays, e.g., when the color chromosomes are given the shape (out line) of the banded chromosomes, yet the composite chromosomes are not banded, is within the scope of the present invention, as well as any registered superposition of banded and color chromosomes is within the scope of the invention.

The chromosome classification method of the present invention as herein described may be employed for various applications some of which are detailed hereinbelow. Following is a brief summary of likely applications of the chromosome classification method of the present invention in the field of molecular cytogenetics. Two major fields of cytogenetics in which the chromosome classification method of the present invention will have considerable impact with particular emphasis on diagnostic applications are (i) clinical cytogenetics and (ii) tumor cytogenetics.

First, the chromosome classification method of the present invention may be used for diagnostic purposes to detect chromosomal aberrations in for example cancerous cells, fetal cells, etc., in a fashion similar to as described in U.S. Pat. No. 5,817,462. About 400,000 cases in both clinical and cancer cytogenetics are analyzed each year in the United States alone, using conventional chromosome banding analysis. Chromosome painting using the classification method of the present invention could be performed in addition to conventional banding analysis and would help to identify marker chromosomes that cannot be characterized using conventional banding alone. Acquired chromosomal aberrations are predominantly associated with malignant transformations. Roughly, two malignancies can be discerned: (i) hematological malignancies and (ii) solid tumors. Since the cells from hematological malignancies are easily cultured in vitro, the chromosome banding analysis of those tumors is one of the success stories in cytogenetic and genetic cancer research. Two well known examples include the identification of the Philadelphia chromosome in chronic lymphatic leukemia (CLL) and a specific chromosomal aberration in Burkitt's lymphoma. Many more tumor specific chromosomal aberrations were described in hematological malignancies in the last decade and are used as a diagnostic and research tool. In many cases the delineation of a recurrent chromosomal aberration has allowed to identify on a molecular basis the mechanism of malignant transformation. Disturbingly, less is known in the field of solid tumors (such as breast, colon, brain lung and others tumors). This discrepancy is even more disturbing because solid tumors play a much higher role in human morbidity than hematological malignancies. The discrepancy is mainly due to technical difficulties common to solid tumor cytogenetics. Solid tumors cells are often difficult to culture, the chromosome preparations are of poor quality, preventing a high resolution cytogenetic analysis, and secondary chromosomal aberration, not necessarily related to tumor initiation or progression are a common feature of these tumors. The availability of a hybridization based chromosomal screening test (i.e., chromosome painting) fills in a methodological gap and is as described above desperately required. Partly, comparative genomic hybridization helps in this respect. However, structural chromosomal aberration cannot be detected and always displays as average of chromosomal aberration in a cell mixture. It is very likely to predict that hybridization based karyotyping would become a widespread method for the delineation of recurrent chromosomal aberrations in solid tumors, both in basic research and in the diagnostic laboratory.

Second, the chromosome classification method of the present invention may be used for comparative cytogenetics [see, J. Weinberg and R. Stanyon (1995) Current opinion in genetics and development 5, 792–797], in a fashion similar to as described in U.S. Pat. No. 5,817,462, to detect and visualize chromosomal rearrangements which changed chromosome morphology during evolution. In the study of evolutionary related species and in the study of model systems (for example mouse as a model system for human) it is in many cases required to obtain comparative genome maps in which chromosomes of two or more species are aligned according to their sequence similarities and thus their chromosome-borne genetic information. Using the chromosome classification method of the present invention will facilitate obtaining such comparative maps.

Consider for example the preparation of a human-mouse chromosome comparative map. For this purpose a complete set of chromosome paints of one of the species (e.g., human) are to be simultaneously hybridized with chromosome spreads of the other species (mouse in the given example) and classified as described above. The result is an image of the mouse karyotype painted with the human chromosome paints. Thus, an alignment can be made between the karyotypes of the two species. In fact cross species hybridization may also be used to create a repetitive color-banding pattern of the analyzed chromosomes. which may assist in cytogenetic analysis of chromosome aberrations. To this end, a lesser number of fluorophores may be employed. For example, using two mouse paints, each includes about half of the mouse chromosomes and is labeled with a distinguishable fluorophore, would yield a two color banding pattern when hybridized with a human chromosome spread.

Third, the chromosome classification method of the present invention may be applied to cells during interphase, mitosis or meiosis. For example, this classification approach may be used to detect interphase chromosome three dimensional arrangements. Little is so far known about the chromosome organization during interphase, yet it is reasonable to suspect that changes occur in the chromosome organization during interphase in malignant cells. Thus, the classification approach of the present invention may be of great value for early detection of various malignancies, defining the stage of a malignant disease, and hence better adjust a treatment to examined patients, etc. It should be noted that Using the classification method of the present invention in combination with a three dimensional reconstruction means (e.g., a confocal microscope) may be used to extract three dimensional information of chromosome organization during interphase, mitosis or meiosis.

Fourth, many cancers and genetic disorders are characterized by chromosome deletions, translocations and other rearrangements and gross abnormalities (e.g., gene amplification). Using the chromosome classification method of the present invention will enhance the ability to detect such abnormalities.

Fifth, one of the common chromosomal aberrations is associated with Down's-syndrome. It was long ago established that Down's syndrome is associated with trisomy of chromosome 21. More careful examination revealed that a specific region of chromosome 21 (21q22) is always associated (i.e., appears in trisomy) with this common syndrome. However, in some cases the karyotype of individuals affected with Down's syndrome is apparently normal as determined by conventional G- or R-banding karyotyping techniques. The widely accepted explanation to this phenomenon is that in these cases the trisomy is of a fragment derived from the 21q22 chromosome region which fragment is small and below the resolution power of the conventional banding techniques. However, using the classification method of the present invention will enable to detect these so far undetectable chromosome 21 trisomies in embryonic cells obtained for example via chorionic villi sampling or from maternal peripheral blood and to enable a more educated genetic counseling to women at high risk. It should be noted that chromosome 13 and chromosome 18 or fragments thereof were also reported to appear in trisomies resulting in birth of strikingly abnormal children and that the classification method of the present invention can be similarly applied for a prenatal diagnosis of these devastating chromosome 13 or 18 trisomies.

Sixth, the classification method of the present invention, combined with the rapidly developing techniques of separating embryonic cells from peripheral blood of a pregnant woman will be of great value for low-risk prenatal karyotyping for the detection of chromosome 21 trisomies and other, less frequent chromosome abnormalities.

Seventh, the classification method of the present invention can be used for the generation of a multicolor banding pattern of chromosomes (i.e., bar-coding, multicolor banding karyotype). For details regarding chromosome bar coding the reader is referred to C. Lengauer et al. (1993) Hum. Molec. Genet. 5, 505–512. The first goal of the human genome project (HGP) is about to be completed. This goal is the generation of a physical map of the human genome. The term "physical map" refers to the cloning of the entire genome in large insert vectors such as YAC-clones or BAC-clones and the mapping of these clones by means of genetic, cytogenetic and physical mapping. Two major sources of human DNA were used or this endeavor, radiation hybrid cell lines and YAC-contigs that contain overlapping clones for all human chromosomes. The completion of this map allows to retrieve for virtually every region in the genome specific clones that are required to identify genes that are causally involved in inherited or acquired genetic diseases including cancer. By combining FISH with multiple YAC- or BAC-clones or radiation hybrids and spectral imaging it is possible to generate a multicolor banding pattern for all human chromosomes that will ultimately link the genetic and the cytogenetic map. As an example, consider the use of a radiation hybrid panel (Stanford panel) [see, Barret J. H. (1992) Genetic mapping based on radiation hybrids. Genomics 13, 95–103]. Each individual panel of the Stanford panel contains a set of DNA fragments with an average fragment size of ca. 5,000 kbp. Each individual panel covers ca. 20% of the human genome. The cohybridization of fluorescent probes derived from five such panels would therefore result in coverage of most of the genome and thus labeling of all human chromosomes. However, the fragments are randomly distributed in the individual panels. Therefore, the number of panels that are required for a complete coverage of the human genome is higher (e.g., 6–10 panels). In the following description assumed is that five individual panels are used. The chromosome fragments of each of the panels are labeled with a different fluorophore (or a different combination of fluorophores, e.g., combinatorial labeling or hybridization strategies) by for example directly incorporating dUTP-conjugated fluorophores using primers derived from interspersed repetitive sequences (IRS, e.g., Alu sequences) in a method known in the art as IRS-PCR approach such as Alu-PCR, which guarantees an exclusive amplification and labeling of human sequences only. If DNA from a species other than human is to be thus amplified and or labeled, a species specific interspersed repetitive sequence (IRS) characterizing the genome of that species is to be used to derive suitable PCR primers. A single separate hybridization of one of the individual panels would give a banding pattern of a chromosome spread in one color with a coverage of about 20% of the genome and an average band size of 5,000 Kbp. Due to the random overlap of individual chromosome fragments in the five hybrid panels, the cohybridization of five differentially labeled groups (each group is represented by a single panel) of fragments would result in a banding pattern including bands that have pure colors, bands that include a combination of two, three, four, as well as five colors each, collectively 31 possible color combinations, which combinations can be distinguished using spectral imaging. The generation of a multicolor high resolution banding pattern of chromosomes has two distinct advantages as compared to the use of chromosome painting probes (i.e., chromosome paints) as follows. Chromosome painting is a well suited tool to detect interchromosomal aberrations such as translocation or homogeneously staining regions as well as additional chromosomes material such as marker chromosomes or double minute chromosomes. Intrachromosomal aberrations such as deletions and duplications would be detected only if the size of the aberrations affect the length of the chromosomes, whereas chromosomal inversions are not detectable at all by this method. However utilizing a multicolor banding pattern, inter- as well as intrachromosomal aberrations could be diagnosed because they would affect the sequence of the chromosomal bands. One major advantage of multicolor high resolution banding pattern using pre-mapped DNA fragments (e.g., YAC-clones and radiation hybrids cell lines) is the possibility to integrate the genetic and the cytogenetic map. Each multicolor band is characterized by a specific set of sequence tagged sites. These are PCR products that occur only once in the genome. Following is a description of the usefulness of the integrated cytogenetic and genetic map. For example, the lack of a specific color band on a chromosome derived from a tumor cell is indicative of a microdeletion that often reflects the loss of a tumor suppressor gene. The knowledge of the sequence target sites (STS's) that are specific for this band would allow to screen any large insert clone collection and retrieve a number of specific clones that are highly likely to contain the gene that is deleted in the described example. It should be mentioned that with the large scale sequencing efforts now underway and with the integration of expressed tagged sites (loci that are known to contain a gene) the value of a hybridization based multicolor banding pattern would increase even more. It is also conceivable that such a multicolor banding pattern could be readily automated. Despite considerable efforts automation of cytogenetic diagnosis based on conventional chromosome bands was so far not successful. The approach described hereinabove will not only be applicable for the generation of a hybridization based banding pattern of human chromosomes but also for other mammalian (e.g., mouse) and non-mammalian species. This will be particularly useful for the analysis in animal models of human diseases including cancer. In analogy to the scenario described for the radiation hybrid panels, a multicolor banding pattern for all human chromosome could be achieved by cohybridization of a set on individual large insert clones such as YAC-clones, PI-clones, BAC-clones or, depending on the resolution that is desired the use of contigs (overlapping clones) from these sources. In further analogy to the use of radiation hybrid panels, a multicolor banding pattern could be introduced by deliberately labeling overlapping clones or contigs with different fluorophores. It will be appreciated by one ordinarily skilled in the art that the retrieval of clones involved in chromosome breakpoints or in chromosomal deletion would be even more straightforward than with the use of radiation hybrid panels. Another source of chromosome fragments suitable for use for multicolor chromosome banding are fragments obtained by microdissection of chromosomes. Microdissected chromosomes fragments are generated by manual or laser micromanipulation of chromosome spreads, as well known in the art. The fragments thus produced are typically multiplied by polymerase chain reaction using for example degenerated oligonucleotides primers (DOP) in a method known in the art as DOP-PCR, or using primers derived from interspersed repetitive sequences (IRS, e.g., Alu sequences) in a method known in the art as IRS-PCR. Yet, an additional source of chromosome fragments suitable for use for multicolor chromosome banding are fragments generated by DNA restriction approaches that generate large DNA fragments and electrophoresis approaches capable of size separating large DNA fragments. As far as generating large DNA fragments by DNA restriction two approaches may be considered. According to the first, a partial digestion by an endonuclease (e.g., frequent or rare cutter) is used, whereas according to the second, a complete digestion by a rare cutter endonuclease (e.g., NotI), is used. The latter is presently preferred, since a complete digestion can be repeated to yield identical results in independent trials, whereas partial digestion is random in nature. Electrophoresis approaches capable of size separating large DNA fragments are well known in the art and include pulse field gel electrophoresis (PFGE). Thus, for example, extracting DNA from consecutive regions along a PFGE lane, labeling the DNA extracted from each of the regions using a different ftluorophore and cohybridizing thus formed probes to chromosomes, would result in a multicolor banding pattern of the chromosomes similarly to as described above. Large DNA fragments may additionally be obtained via gradient centrifugation such as sucrose or cesium chloride gradients as well known in the art. Nevertheless, it will be appreciated that using these approaches do not provide a possibility to integrate the genetic and the cytogenetic map as described above and is therefore presently less favorable.

The generation of a multicolor banding pattern of chromosomes (i.e., multicolor banding karyotype) based on fluorescent in situ hybridization and the chromosome classification method of the present invention can be used for various practical applications. These include for example (i) screen for chromosomal aberrations using for example specifically tailored clone sets; (ii) screening for telomeric deletions, which are otherwise difficult of detection; (iii) screening for chromosomal aneuploidies during prenatal diagnosis; (iv) screening for recurrent chromosomal breakpoints; (v) multicolor comparative genomic hybridization; (vii) combining multicolor FISH with other measurements of cytological and immunohistochemical stains for multiparameter analysis of tumor cells; (viii) combining multicolor banding patterns with conventional R- or G-bands; (ix) analysis of genetic aberrations directly in interphase cells; and (x) screening for chromosomal aberrations in radiation or mutagen exposed populations.

The major advantage of the method of the present invention is the introduction of a method for chromosome classification which uses internal reference vectors for pixels classification, which internal reference vectors typically perform better. Another advantage of the present invention is that the method is readily automated. Using this method will therefore enable semi or non-skilled cytogenetecists to acquire clear and informative karyotypes, which may include overlay of spectral and spatial information.

While the invention has been described with respect to a limited number of embodiments, it will be appreciated that many variations, modifications and other applications of the invention may be made.

What is claimed is:

1. A method for finding L internal reference vectors for classification of L chromosomes or portions of chromosomes of a cell, the L chromosomes or portions of chromosomes being painted with K different fluorophores or combinations thereof, wherein K basic chromosomes or portions of chromosomes are each painted with only one of the K different fluorophores, whereas the other L-K of the L chromosomes or portions of chromosomes are each painted with a different combination of the K different fluorophores, the method comprising the steps of:

(a) using a multi-band collection device for measuring a first vector for each pixel of each of the L chromosomes or portions of chromosomes;

(b) identifying pixels belonging to each of the K basic chromosomes or portions of chromosomes and defining said pixels as basic pixels, so as to obtain K basic classes of basic pixels;

(c) using at least one basic pixel from each of said K basic classes for obtaining K basic vectors, said K basic vectors being K internal reference vectors;

(d) using said K basic vectors for identifying pixels belonging to the other L-K chromosomes or portions of chromosomes; and (e) using said pixels belonging to the other L-K chromosomes or portions of chromosomes for calculating the other L-K internal reference vectors, thereby finding all of the L internal reference vectors.

2. The method of claim 1, wherein multi-band collection device is selected from the group consisting of a spectral imager and a device including a plurality of filter cubes.

3. The method of claim 1, wherein for each said pixel said first vector includes N items, N is an integer selected in the range of 3–150.

4. The method of claim 1, wherein for each said pixel said first vector represents a spectrum.

5. The method of claim 1, wherein for each said pixel said first vector is normalized.

6. The method of claim 1, wherein said identification of said pixels belonging to each of the K basic chromosomes or portions of chromosomes is effected by a method selected from the group consisting of:

(a) identifying said pixels belonging to each of the K basic chromosomes or portions of chromosomes using a conventional banding pattern of the L chromosomes or portions of chromosomes;

(b) identifying said pixels belonging to each of the K basic chromosomes or portions of chromosomes using an RGB algorithm; and (c) identifying said pixels belonging to each of the K basic chromosomes or portions of chromosomes using K external basic vectors from a library.

7. The method of claim 1, wherein each of said K basic vectors is an average of a plurality of basic pixels belonging to one of said basic classes.

8. As The method of claim 6, wherein said identification of said pixels belonging to each of the K basic chromosomes or portions of chromosomes using said external basic vectors from said library is effected by:

(a) employing a linear decomposition algorithm for defining for each pixel of said L chromosomes or portions of chromosomes a decomposition-K-vector;

(b) using a high cut off value, for transforming each of said decomposition-K-vector into a transformed binary-K-vector; and (c) comparing each of said transformed binary-K-vector to K defined binary-K-vectors, defining each of the K different fluorophores, thereby identifying said pixels belonging to each of the K basic chromosomes or portions of chromosomes.

9. The method of claim 1, wherein said cell is of a human being.

10. The method of claim 1, wherein said identification of said pixels belonging to the other L-K chromosomes or portions of chromosomes and calculating the other L-K internal reference vectors is effected by:

(a) employing a linear decomposition algorithm for defining for each pixel of said L chromosomes or portions of chromosomes a decomposition-K-vector;

(b) using a low cut off value or range, for transforming each of said decomposition-K-vector into a transformed binary-K-vector; and (c) comparing each of said transformed binary-K-vector to L-K defined binary-K-vectors, defining each of the combinations of the K different fluorophores, thereby identifying said pixels belonging to each of the L-K chromosomes or portions of chromosomes.

11. A method for classification of L chromosomes or portions of chromosomes of a cell, the L chromosomes or portions of chromosomes being painted with K different fluorophores or combinations thereof, wherein K basic chromosomes or portions of chromosomes are each painted with only one of the K different fluorophores, whereas the other L-K of the L chromosomes or portions of chromosomes are each painted with a different combination of the K different fluorophores, the method comprising the steps of:

(a) finding L internal reference vectors by:
  (i) using a multi-band collection device for measuring a first vector for each pixel of each of the L chromosomes or portions of chromosomes;
  (ii) identifying pixels belonging to each of the K basic chromosomes or portions of chromosomes and defining said pixels as basic pixels, so as to obtain K basic classes of basic pixels;
  (iii) using at least one basic pixel from each of said K basic classes for obtaining K basic vectors, said K basic vectors being K internal reference vectors;
  (iv) using said K basic vectors for identifying pixels belonging to the other L-K chromosomes or portions of chromosomes; and
  (v) using said pixels belonging to the other L-K chromosomes or portions of chromosomes for calculating the other L-K internal reference vectors, thereby finding all of the L internal reference vectors; and (b) using said L reference vectors for classification of each of said pixels into one of L classification classes.

12. A method for classification of L chromosomes or portions of chromosomes of a cell, the L chromosomes or portions of chromosomes being painted with K different fluorophores or combinations thereof, wherein K basic chromosomes or portions of chromosomes are each painted with only one of the K different fluorophores, whereas the other L-K of the L chromosomes or portions of chromosomes are each painted with a different combination of the K different fluorophores, the method comprising the steps of:

(a) using a multi-band collection device for measuring a first vector for each pixel of each of the L chromosomes or portions of chromosomes;

(b) identifying pixels belonging to each of the K basic chromosomes or portions of chromosomes and defining said pixels as basic pixels, so as to obtain K basic classes of basic pixels;

(c) using at least one basic pixel from each of said K basic classes for obtaining K basic vectors, said K basic vectors being K internal reference vectors; and (d) using said K basic vectors for identifying pixels belonging to the other L-K chromosomes or portions of chromosomes.

13. A method for classification of chromosomes or portions of chromosomes of a cell, the chromosomes or portions of chromosomes being painted with different fluorophores or combinations thereof, such that each of the chromosomes or portions of chromosomes is painted with a different fluorophore or combination of fluorophores, the method comprising the steps of:

(a) using a multi-band collection device for measuring a first vector for each pixel of each of the chromosomes or portions of chromosomes;

(b) identifying pixels belonging to basic chromosomes or portions of chromosomes and defining said pixels as basic pixels, so as to obtain basic classes of basic pixels;

(c) using at least one basic pixel from each of said basic classes for obtaining basic vectors, said basic vectors being basic internal reference vectors; and (d) using said basic internal reference vectors for identifying pixels belonging to the other chromosomes or portions of chromosomes.

14. The method of claim 11, further comprising the step of attributing each of said classes of classified pixels a distinctive artificial color.

15. The method of claim 11, wherein said multi-band collection device is selected from the group consisting of a spectral imager and a device including a plurality of filter cubes.

16. The method of claim 11, wherein for each said pixel said first vector includes N items, N is an integer selected in the range of 3–150.

17. The method of claim 11, wherein for each said pixel said first vector represents a spectrum.

18. The method of claim 11, wherein for each said pixel said first vector is normalized.

19. The method of claim 11, wherein said identification of said pixels belonging to each of the K basic chromosomes or portions of chromosomes is effected by a method selected from the group consisting of:

(a) identifying said pixels belonging to each of the K basic chromosomes or portions of chromosomes using a conventional banding pattern of the L chromosomes or portions of chromosomes;

(b) identifying said pixels belonging to each of the K basic chromosomes or portions of chromosomes using an RGB algorithm; and (c) identifying said pixels belonging to each of the K basic chromosomes or portions of chromosomes using K external basic vectors from a library.

20. The method of claim 11, wherein each of said K basic vectors is an average of a plurality of basic pixels belonging to one of said basic classes.

21. The method of claim 19, wherein said identification of said pixels belonging to each of the K basic chromosomes or portions of chromosomes using said external basic vectors from said library is effected by:

(a) employing a linear decomposition algorithm for defining for each pixel of said L chromosomes or portions of chromosomes a decomposition-K-vector;

(b) using a high cut off value, for transforming each of said decomposition-K-vector into a transformed binary-K-vector; and (c) comparing each of said transformed binary-K-vector to K defined binary-K-vectors, defining each of the K different fluorophores, thereby identifying said pixels belonging to each of the K basic chromosomes or portions of chromosomes.

22. The method of claim 11, wherein said classification of each of said pixels into one of said L classification classes using said L reference vectors is effected by a linear decomposition algorithm used for finding binary vectors for each of said pixels belonging to the L chromosomes or portions of chromosomes.

23. The method of claim 11, wherein said identification of said pixels belonging to the other L-K chromosomes or portions of chromosomes and calculating the other L-K internal reference vectors is effected by:
   (a) employing a linear decomposition algorithm for defining for each pixel of said L chromosomes or portions of chromosomes a decomposition-K-vector;
   (b) using a low cut off value or range, for transforming each of said decomposition-K-vector into a transformed binary-K-vector; and
   (c) comparing each of said transformed binary-K-vector to L-K defined binary-K-vectors, defining each of the combinations of the K different fluorophores, thereby identifying said pixels belonging to each of the L-K chromosomes or portions of chromosomes.

24. The method of claim 11, wherein said cell is of a human being.

25. A process for detection of chromosome aberrations using a method for classification of L chromosomes or portions of chromosomes of a cell, the L chromosomes or portions of chromosomes being painted with K different fluorophores or combinations thereof, wherein K basic chromosomes or portions of chromosomes are each painted with only one of the K different fluorophores, whereas the other L-K of the L chromosomes or portions of chromosomes are each painted with a different combination of the K different fluorophores, the method comprising the steps of:
   (a) finding L internal reference vectors by:
      (i) using a multi-band collection device for measuring a first vector for each pixel of each of the L chromosomes or portions of chromosomes;
      (ii) identifying pixels belonging to each of the K basic chromosomes or portions of chromosomes and defining said pixels as basic pixels, so as to obtain K basic classes of basic pixels;
      (iii) using at least one basic pixel from each of said K basic classes for obtaining K basic vectors, said K basic vectors being K internal reference vectors;
      (iv) using said K basic vectors for identifying pixels belonging to the other L-K chromosomes or portions of chromosomes; and
      (v) using said pixels belonging to the other L-K chromosomes or portions of chromosomes for calculating the other L-K internal reference vectors, thereby finding all of the L internal reference vectors; and
   (b) using said L reference vectors for classification of each of said pixels into one of L classification classes.

* * * * *